US010466228B2

(12) United States Patent
Ikeda et al.

(10) Patent No.: US 10,466,228 B2
(45) Date of Patent: Nov. 5, 2019

(54) NANO-GAP ELECTRODE PAIR AND METHOD OF MANUFACTURING SAME

(71) Applicant: Quantum Biosystems Inc., Tokyo (JP)

(72) Inventors: Shuji Ikeda, Tokyo (JP); Mark Oldham, Emerald Hills, CA (US); Eric S. Nordman, Palo Alto, CA (US)

(73) Assignee: QUANTUM BIOSYSTEMS INC., Tokyo (JP)

(\*) Notice: Subject to any disclaimer, the term of this patent is extended or adjusted under 35 U.S.C. 154(b) by 0 days.

(21) Appl. No.: 16/178,924

(22) Filed: Nov. 2, 2018

(65) Prior Publication Data

US 2019/0310240 A1 Oct. 10, 2019

Related U.S. Application Data

(63) Continuation of application No. 15/098,147, filed on Apr. 13, 2016, now Pat. No. 10,261,066, which is a
(Continued)

(30) Foreign Application Priority Data

Oct. 16, 2013 (JP) ................. 2013-215828

(51) Int. Cl.
*G01N 27/447* (2006.01)
*G01N 33/487* (2006.01)
(Continued)

(52) U.S. Cl.
CPC . *G01N 33/48721* (2013.01); *C23C 16/45525* (2013.01); *G01N 27/3278* (2013.01); *G01N 27/44791* (2013.01)

(58) Field of Classification Search
CPC ....... G01N 33/48721; G01N 27/44791; G01N 27/3278; G01N 27/4473; C23C 16/45525;
(Continued)

(56) References Cited

U.S. PATENT DOCUMENTS 5,092,972 A 3/1992 Ghowsi
5,122,248 A 6/1992 Karger et al.
(Continued)

FOREIGN PATENT DOCUMENTS

CN 1828849 A 9/2006
CN 101046458 A 10/2007
(Continued)

OTHER PUBLICATIONS

Co-pending U.S. Appl. No. 16/266,363, filed Feb. 4, 2019.
(Continued)

*Primary Examiner* — Gurpreet Kaur
(74) *Attorney, Agent, or Firm* — Wilson Sonsini Goodrich & Rosati

(57) ABSTRACT

A system for detecting a biomolecule comprises a nano-gap electrode device including a first electrode and a second electrode adjacent to the first electrode. The first electrode can be separated from the second electrode by a nano-gap that is dimensioned to permit the biomolecule to flow through the nano-gap. The nano-gap can have at least a first gap region and a second gap region. The second gap region can be oriented at an angle that is greater than zero degrees with respect to a plane having the first gap region. The system can further include an electrical circuit coupled to the nano-gap electrode device. The electrical circuit can receive electrical signals from the first electrode and the second electrode upon the flow of the biomolecule through the nano-gap.

20 Claims, 15 Drawing Sheets

Related U.S. Application Data continuation of application No. PCT/US2014/060742, filed on Oct. 15, 2014.

(51) Int. Cl.
*C23C 16/455* (2006.01)
*G01N 27/327* (2006.01)

(58) Field of Classification Search
CPC .. C12Q 1/6813; C12Q 1/6876; C12Q 1/6825; C12Q 1/6869; Y10S 977/852; Y10S 977/733; Y10S 977/72; Y10S 977/721; B82Y 5/00; B82Y 15/00
See application file for complete search history.

(56) References Cited

U.S. PATENT DOCUMENTS

| | | |
|---|---|---|
| 5,151,164 A | 9/1992 | Blanchard et al. |
| 5,262,031 A | 11/1993 | Lux et al. |
| 5,329,236 A | 7/1994 | Gemma et al. |
| 5,593,838 A | 1/1997 | Zanzucchi et al. |
| 5,906,723 A | 5/1999 | Mathies et al. |
| 6,159,353 A | 12/2000 | West et al. |
| 6,447,663 B1 | 9/2002 | Lee et al. |
| 6,491,805 B1 | 12/2002 | Gordon et al. |
| 6,613,513 B1 | 9/2003 | Parce et al. |
| 6,905,586 B2 | 6/2005 | Lee et al. |
| 7,033,476 B2 | 4/2006 | Lee et al. |
| 7,468,271 B2 | 12/2008 | Golovchenko et al. |
| 7,892,414 B1 | 2/2011 | Sumner |
| 7,918,979 B2 | 4/2011 | Han et al. |
| 8,105,471 B1 | 1/2012 | Han et al. |
| 8,333,934 B2 | 12/2012 | Cao et al. |
| 8,652,779 B2 | 2/2014 | Turner et al. |
| 9,194,838 B2 | 11/2015 | Taniguchi et al. |
| 9,506,894 B2 | 11/2016 | Kawai et al. |
| 9,535,033 B2 | 1/2017 | Kawai et al. |
| 9,644,236 B2 | 5/2017 | Kawai et al. |
| 10,202,644 B2 | 2/2019 | Taniguchi et al. |
| 10,261,066 B2 | 4/2019 | Ikeda et al. |
| 2001/0046681 A1 | 11/2001 | Senapathy |
| 2002/0046953 A1 | 4/2002 | Lee et al. |
| 2002/0081744 A1 | 6/2002 | Chan et al. |
| 2002/0168671 A1 | 11/2002 | Burns et al. |
| 2002/0168810 A1 | 11/2002 | Jackson |
| 2003/0052006 A1 | 3/2003 | Noca et al. |
| 2003/0075445 A1 | 4/2003 | Woudenberg et al. |
| 2003/0085719 A1 | 5/2003 | Yoon et al. |
| 2003/0089606 A1 | 5/2003 | Parce et al. |
| 2003/0104428 A1 | 6/2003 | Branton et al. |
| 2003/0141189 A1 | 7/2003 | Lee et al. |
| 2003/0207326 A1 | 11/2003 | Su et al. |
| 2004/0124084 A1 | 7/2004 | Lee et al. |
| 2004/0144658 A1 | 7/2004 | Flory |
| 2004/0161708 A1 | 8/2004 | Nagase et al. |
| 2005/0048513 A1 | 3/2005 | Harwit et al. |
| 2005/0051768 A1 | 3/2005 | Kim et al. |
| 2005/0061669 A1 | 3/2005 | Woudenberg et al. |
| 2005/0084865 A1 | 4/2005 | Yu et al. |
| 2005/0112860 A1 | 5/2005 | Park et al. |
| 2005/0127035 A1 | 6/2005 | Ling et al. |
| 2005/0136419 A1 | 6/2005 | Lee |
| 2005/0202444 A1 | 9/2005 | Zhu |
| 2005/0202446 A1 | 9/2005 | Yang et al. |
| 2005/0227239 A1 | 10/2005 | Joyce |
| 2006/0011480 A1 | 1/2006 | Sano et al. |
| 2006/0057585 A1 | 3/2006 | McAllister |
| 2006/0071209 A1 | 4/2006 | Flory et al. |
| 2006/0154399 A1 | 7/2006 | Sauer et al. |
| 2006/0154400 A1 | 7/2006 | Choi et al. |
| 2006/0210995 A1 | 9/2006 | Joyce |
| 2006/0275911 A1 | 12/2006 | Wang et al. |
| 2007/0029911 A1 | 2/2007 | Hudspeth et al. |
| 2007/0042366 A1 | 2/2007 | Ling |
| 2007/0171714 A1 | 7/2007 | Wu et al. |
| 2007/0183198 A1 | 8/2007 | Otsuka et al. |
| 2008/0077607 A1 | 3/2008 | Gatawood et al. |
| 2008/0119366 A1 | 5/2008 | Sauer et al. |
| 2008/0171316 A1 | 7/2008 | Golovchenko et al. |
| 2008/0202931 A1 | 8/2008 | Petsev et al. |
| 2008/0215252 A1 | 9/2008 | Kawai et al. |
| 2008/0248561 A1 | 10/2008 | Golovchenko et al. |
| 2009/0023146 A1 | 1/2009 | Harnack et al. |
| 2009/0155917 A1 | 6/2009 | Umezawa et al. |
| 2009/0215156 A1 | 8/2009 | Chung et al. |
| 2009/0229854 A1 | 9/2009 | Fredenberg et al. |
| 2009/0242429 A1 | 10/2009 | Sitdikov et al. |
| 2009/0283412 A1 | 11/2009 | Sansinena et al. |
| 2009/0286936 A1 | 11/2009 | Ogata et al. |
| 2009/0305273 A1 | 12/2009 | Cao et al. |
| 2010/0025249 A1 | 2/2010 | Polonsky et al. |
| 2010/0066348 A1 | 3/2010 | Merz et al. |
| 2010/0084276 A1 | 4/2010 | Lindsay et al. |
| 2010/0184062 A1 | 7/2010 | Steinmuller-Nethl et al. |
| 2010/0188109 A1 | 7/2010 | Edel et al. |
| 2010/0243449 A1 | 9/2010 | Oliver |
| 2010/0267158 A1 | 10/2010 | Chou et al. |
| 2010/0292101 A1 | 11/2010 | So |
| 2010/0331194 A1 | 12/2010 | Turner et al. |
| 2011/0056845 A1 | 3/2011 | Stellacci et al. |
| 2011/0171634 A1 | 7/2011 | Xiao et al. |
| 2011/0179852 A1 | 7/2011 | Polonsky et al. |
| 2011/0181150 A1 | 7/2011 | Mahameed et al. |
| 2011/0193183 A1 | 8/2011 | Agarwal et al. |
| 2011/0236984 A1 | 9/2011 | Sun et al. |
| 2011/0250464 A1 | 10/2011 | Wilson et al. |
| 2011/0287956 A1 | 11/2011 | Iqbal et al. |
| 2012/0041727 A1 | 2/2012 | Mishra et al. |
| 2012/0097539 A1 | 4/2012 | Qian et al. |
| 2012/0132886 A1 | 5/2012 | Peng et al. |
| 2012/0184047 A1 | 7/2012 | Jonsson et al. |
| 2012/0193237 A1 | 8/2012 | Afzali-Ardakani et al. |
| 2012/0199485 A1 | 8/2012 | Sauer et al. |
| 2012/0254715 A1 | 10/2012 | Schwartz et al. |
| 2012/0298511 A1 | 11/2012 | Yamamoto |
| 2012/0322055 A1 | 12/2012 | Royyuru |
| 2013/0001082 A1 | 1/2013 | Afzali-Ardakani et al. |
| 2013/0092547 A1 | 4/2013 | Li et al. |
| 2013/0157271 A1 | 6/2013 | Coursey et al. |
| 2013/0186758 A1 | 7/2013 | Saha et al. |
| 2013/0264207 A1 | 10/2013 | Ju et al. |
| 2013/0334047 A1 | 12/2013 | Jeong et al. |
| 2014/0000105 A1 | 1/2014 | Bielick et al. |
| 2014/0008225 A1 | 1/2014 | Jeon et al. |
| 2014/0031995 A1 | 1/2014 | Kawai et al. |
| 2014/0055150 A1 | 2/2014 | Kawai et al. |
| 2014/0103945 A1 | 4/2014 | Eid et al. |
| 2014/0183040 A1 | 7/2014 | Kawai et al. |
| 2014/0202857 A1 | 7/2014 | Valbusa et al. |
| 2014/0273186 A1 | 9/2014 | Oxenrider |
| 2014/0300339 A1 | 10/2014 | Taniguchi et al. |
| 2014/0302675 A1 | 10/2014 | Astier et al. |
| 2014/0364324 A1 | 12/2014 | Turner et al. |
| 2014/0374695 A1 | 12/2014 | Astier et al. |
| 2015/0107996 A1 | 4/2015 | Chen |
| 2015/0111759 A1 | 4/2015 | Ju et al. |
| 2015/0132756 A1 | 5/2015 | Peter et al. |
| 2015/0219593 A1 | 8/2015 | Kawai et al. |
| 2015/0310228 A1 | 10/2015 | Benz et al. |
| 2015/0323490 A1 | 11/2015 | Luan et al. |
| 2016/0048690 A1 | 2/2016 | Tanishima et al. |
| 2016/0049327 A1 | 2/2016 | Singh et al. |
| 2016/0138101 A1 | 5/2016 | Taniguchi et al. |
| 2016/0245789 A1 | 8/2016 | Ikeda et al. |
| 2016/0245790 A1 | 8/2016 | Kawai et al. |
| 2016/0320364 A1 | 11/2016 | Ikeda et al. |
| 2016/0377591 A1 | 12/2016 | Kawai et al. |
| 2017/0131237 A1 | 5/2017 | Ikeda |
| 2017/0144158 A1 | 5/2017 | Taniguchi |
| 2017/0146510 A1 | 5/2017 | Ikeda et al. |
| 2017/0146511 A1 | 5/2017 | Taniguchi et al. |
| 2017/0306396 A1 | 10/2017 | Kawai et al. |
| 2018/0023132 A1 | 1/2018 | Kawai et al. |

(56) References Cited

U.S. PATENT DOCUMENTS

FOREIGN PATENT DOCUMENTS

| | | |
|---|---|---|
| CN | 101920932 A | 12/2010 |
| CN | 102180440 A | 9/2011 |
| CN | 102753708 A | 10/2012 |
| CN | 102914395 A | 2/2013 |
| CN | 103203256 A | 7/2013 |
| CN | 103502795 A | 1/2014 |
| EP | 1419112 A1 | 5/2004 |
| EP | 2573554 A1 | 3/2013 |
| JP | 62-194673 A | 8/1987 |
| JP | S6437640 A | 2/1989 |
| JP | 04-302151 A | 10/1992 |
| JP | H04302151 A | 10/1992 |
| JP | H0774337 A | 3/1995 |
| JP | H10283230 A | 10/1998 |
| JP | 2003507026 A | 2/2003 |
| JP | 2003090815 A | 3/2003 |
| JP | 2003332555 A | 11/2003 |
| JP | 2003533676 A | 11/2003 |
| JP | 2004233356 A | 8/2004 |
| JP | 2004247203 A | 9/2004 |
| JP | 2004303162 A | 10/2004 |
| JP | 2005501234 A | 1/2005 |
| JP | 2005257687 A | 9/2005 |
| JP | 2006078491 A | 3/2006 |
| JP | 2006526777 A | 11/2006 |
| JP | 2007272212 A | 10/2007 |
| JP | 2008032529 A | 2/2008 |
| JP | 2008146538 A | 6/2008 |
| JP | 4128573 B2 | 7/2008 |
| JP | 2008186975 A | 8/2008 |
| JP | 2008536124 A | 9/2008 |
| JP | 4289938 B2 | 7/2009 |
| JP | 2009527817 A | 7/2009 |
| JP | 2009210272 A | 9/2009 |
| JP | 2009272432 A | 11/2009 |
| JP | 2010510476 A | 4/2010 |
| JP | 2010513853 A | 4/2010 |
| JP | 2010227735 A | 10/2010 |
| JP | 2011500025 A | 1/2011 |
| JP | 2011054631 A | 3/2011 |
| JP | 2011516050 A | 5/2011 |
| JP | 4719906 B2 | 7/2011 |
| JP | 2011163934 A | 8/2011 |
| JP | 2011211905 A | 10/2011 |
| JP | 2012110258 A | 6/2012 |
| JP | 2012118709 A | 6/2012 |
| JP | 2013036865 A | 2/2013 |
| JP | 2013090576 A | 5/2013 |
| JP | 2013518283 A | 5/2013 |
| JP | 2013519074 A | 5/2013 |
| JP | 2013215725 A | 10/2013 |
| JP | 2014074599 A | 4/2014 |
| JP | 2014173936 A | 9/2014 |
| JP | 2015059824 A | 3/2015 |
| JP | 2015077652 A | 4/2015 |
| KR | 1020140031559 | 3/2014 |
| TW | 200619614 A | 6/2006 |
| TW | 200637916 A | 11/2006 |
| TW | 200907068 A | 2/2009 |
| TW | 201013179 A | 4/2010 |
| TW | 201100796 A | 1/2011 |
| WO | WO-0113088 A1 | 2/2001 |
| WO | WO-0181896 A1 | 11/2001 |
| WO | WO-0181908 A1 | 11/2001 |
| WO | WO-03018484 A1 | 3/2003 |
| WO | WO-03042396 A2 | 5/2003 |
| WO | WO-03106693 A2 | 12/2003 |
| WO | WO-2007013370 A1 | 2/2007 |
| WO | WO-2008071982 A2 | 6/2008 |
| WO | WO-2008071982 A3 | 7/2008 |
| WO | WO-2008079169 A2 | 7/2008 |
| WO | WO-2009045472 A1 | 4/2009 |
| WO | WO-2009093019 A2 | 7/2009 |
| WO | WO-2009120642 A1 | 10/2009 |
| WO | WO-2009149362 A2 | 12/2009 |
| WO | WO-2010111605 A2 | 9/2010 |
| WO | WO-2010116595 A1 | 10/2010 |
| WO | WO-2010111605 A3 | 11/2010 |
| WO | WO-2011082419 A2 | 7/2011 |
| WO | WO-2011097171 A1 | 8/2011 |
| WO | WO-2011108540 A1 | 9/2011 |
| WO | WO-2012009578 A2 | 1/2012 |
| WO | WO-2012009578 A3 | 4/2012 |
| WO | WO-2012164679 A1 | 12/2012 |
| WO | WO-2012170560 A2 | 12/2012 |
| WO | WO-2013016486 A1 | 1/2013 |
| WO | WO-2013066456 A2 | 5/2013 |
| WO | WO-2013074546 A1 | 5/2013 |
| WO | WO-2013076943 A1 | 5/2013 |
| WO | WO-2013066456 A3 | 7/2013 |
| WO | WO-2013100949 A1 | 7/2013 |
| WO | WO-2013115185 A1 | 8/2013 |
| WO | WO-2013116509 A1 | 8/2013 |
| WO | WO-2013147208 A1 | 10/2013 |
| WO | WO-2014027580 A1 | 2/2014 |
| WO | WO-2014084931 A1 | 6/2014 |
| WO | WO-2015028885 A2 | 3/2015 |
| WO | WO-2015028886 A2 | 3/2015 |
| WO | WO-2015042200 A1 | 3/2015 |
| WO | WO-2015028885 A3 | 4/2015 |
| WO | WO-2015057870 A1 | 4/2015 |
| WO | WO-2015028886 A3 | 5/2015 |
| WO | WO-2015111760 A1 | 7/2015 |
| WO | WO-2015125920 A1 | 8/2015 |
| WO | WO-2015167019 A1 | 11/2015 |
| WO | WO-2015170782 A1 | 11/2015 |
| WO | WO-2015170783 A1 | 11/2015 |
| WO | WO-2015170784 A1 | 11/2015 |
| WO | WO-2016206593 A1 | 12/2016 |
| WO | WO-2017061129 A1 | 4/2017 |
| WO | WO-2017179581 A1 | 10/2017 |
| WO | WO-2017189930 A1 | 11/2017 |
| WO | WO-2018025887 A1 | 2/2018 |
| WO | WO-2019065904 A1 | 4/2019 |

OTHER PUBLICATIONS

U.S. Appl. No. 15/098,147 Notice of Allowance dated Mar. 6, 2019.
Co-pending U.S. Appl. No. 16/234,908, filed Dec. 28, 2018.
U.S. Appl. No. 15/098,147 Notice of Allowance dated Dec. 28, 2018.
U.S. Appl. No. 15/098,147 Notice of Allowance dated Nov. 28, 2018.
U.S. Appl. No. 15/098,147 Office Action dated Jul. 10, 2018.
Anima et al. Fabrications of insulator-protected nanometer-sized electrode gaps. Journal of Applied Physics 115:114310 (2014). 6 pages. doi: 10.1063/1.4869135.
Armbrust et al. Clearing the clouds away from the true potential and obstacles posed by this computing capability. Communications of the ACM 53(4):50-58 (Apr. 2010).
Axopatch 2008 Patch Clamp: Theory and Operation, Axon Instruments, Inc., Mar. 1999.
Bagci, et al. Recognizing nucelotides by cross-tunneling currents for DNA sequencing. Physical Review E, vol. 84, Issue No. 1, Article No. 011917 (internal pp. 1-4) (2011).
Brown, et al. Nucleotide-Surface Interactions in DNA-Modified Au-Nanoparticle Conjugates: Sequence Effects on Reactivity and Hybridization. J. Phys. Chem. C, 2008, 112 (20), pp. 7517-7521.
Carter, et al. Voltammetric studies of the interaction of metal chelates with DNA. 2. Tris-chelated complexes of cobalt (III) and iron (II) with 1, 10-phenanthroline and 2, 2'-bipyridine. Journal of the American Chemical Society 111.24 (1989): 8901-8911.
Chang, et al. Tunnelling readout of hydrogen-bonding-based recognition. Nature Nantechnology, vol. 4, May 2009, pp. 297-301.
Chen, et al., A novel nanofabrication technique for the array of Nanogap electrodes, Japanese Journal of Applied Physics, Japan Society of Applied physics, JP, 2006, 45(6):5531-5534.
Chen, et al., Probing Single DNA Molecule Transport Using Fabricated Nanopores, Nano Letters, 2004, 4(11):2293-2298.

(56) References Cited

OTHER PUBLICATIONS

Cheng, et al. Development of an electrochemical membrane-based nanobiosensor for ultrasensitive detection of dengue virus. Anal Chim Acta. May 6, 2012;725:74-80. doi: 10.1016/j.aca.Mar. 17, 2012. Epub Mar. 17, 2012.
Clarke, et al. Continuous base identification for single-molecule nanopore DNA sequencing. Nat Nanotechnol. Apr. 2009;4(4):265-70. doi: 10.1038/nnano.Dec. 2009. Epub Feb. 22, 2009.
Co-pending U.S. Appl. No. 14/687,856, filed Apr. 15, 2015.
Co-pending U.S. Appl. No. 14/883,494, filed Oct. 14, 2015.
Co-pending U.S. Appl. No. 15/448,317, filed Mar. 2, 2017.
Co-pending U.S. Appl. No. 15/937,327, filed Mar. 27, 2018.
Co-pending U.S. Appl. No. 16/156,755, filed Oct. 10, 2018.
Co-pending U.S. Appl. No. 16/169,756, filed Oct. 24, 2018.
Dekker, et al. Solid-state nanopores. Nature Nanotechnology, vol. 2, Apr. 2007, pp. 209-215.
Ei-Ali, et al., Simulation and experimental validation of a SU-8 based PCR themorcycler chp with integrated heaters and temperature sensor, Sensors and Actuators A, 110, 2004, pp. 3-10.
EP 14854676.5 Extended European Search Report and Search Opinion dated Apr. 26, 2017.
European search report and opinion dated Apr. 8, 2016 for EP Application No. 13879507.5.
Feng et al. "Nanopore-based Fourth-generation DNA Sequencing Technology" Genomics, Proteomics & Bioinformatics. 2015; 13(1):4-16, p. 5, col2, para 3.
Fischbein, et al. Sub-10 nm Device Fabrication in a Transmission Electron Microscope. American Chemical Society, Nano Letters, 2007, vol. 7, No. 5, pp. 1329-1337.
Fologea, et al. Detecting Single Stranded DNA with a Solid State Nanopore. American Chemical Society, Nano Letters, 2005, vol. 5, No. 10, pp. 1905-1909.
Fuller et al. "Real-time single-molecule electronic DNA sequencing by synthesis using polymer-tagged nucleotides on a nanopore array" PNAS, Mar. 18, 2016 (Mar. 18, 2016); 113(19):5233-5238 (doi: 10.1073/pnas.1601782113) p. 5234, col. 1, para 1-3; p. 5235, col. 1, para 1; p. 5236, col. 1, para 1; Fig. 2.
Furuhashi et al. Denaturation of DNAs in a nanofluidic channel by micro-heating method. The 74th Annual Meeting of the Japan Society of Applied Physics Lecture Papers p. 12-295 (Aug. 2013).
Furuhashi et al. Denature of double-stranded DNAs by a micro-heating method. Proceedings of the 60th Spring Science Lecture Meeting of the Japan Society of Applied Physics, p. 12-356, (Mar. 2013).
Furuhashi, et al. High speed DNA denaturation using microheating devices. Appl. Phys. Lett., Jul. 11, 2013, 103, pp. 023112.
Garcia-Lekue et al. Plane-wave-based electron tunneling through Au nanojunctions: Numerical calculations. Physical Review B 82:035410 (2010). 9 pages.
Gierhart, et al. Nanopore with transverse nanoelectrodes for electrical characterization and sequencing of DNA. Sens Actuators B Chem. Jun. 16, 2008;132(2):593-600.
Gonzalez, et al. Mass transport effect of mesoscopic domains in the amperometric response of an electroactive species: Modeling for its applications in biomolecule detection. Sensors and Actuators B: Chemical 144.2 (2010): 349-353.
Hashioka, et al, Metal nanogap devices fabricated by conventional photolithography and their application to deoxyribose nucleic acid analysis, Journal of Vacuum Science & Technology B: microelectronics; Materials, Processing and Phenomena, 2003, 21(6):2937-40.
He, et al. Controlling DNA translocation through gate modulation of nanopore wall surface charges. ACS Nano. Jul. 26, 2011;5(7):5509-18. doi: 10.1021/nn201883b. Epub Jun. 17, 2011.
He, et al. Gate manipulation of DNA capture into nanopores. ACS Nano. Oct. 25, 2011;5(10):8391-7. doi: 10.1021/nn203186c. Epub Sep. 26, 2011.
He, et al. Identification of DNA Basepairing via Tunnel-Current Decay. American Chemical Society, Nano Letters, 2007, vol. 7, No. 12, pp. 3854-3858.
He, et al. Thermophoretic manipulation of DNA translocation through nanopores. ACS Nano. Jan. 22, 2013;7(1):538-46. doi: 10.1021/nn304914j. Epub Dec. 10, 2012.
Healy et al. Fabrication and characterization of nanopores with insulated transverse nanoelectrodes for DNA sensing in salt solution. Electrophoresis 33(23) (Dec. 2012). doi: 10.1002/elps.201200350. 15 pages.
Huang, et al. Identifying single bases in a DNA oligomer with electron tunnelling. Nat Nanotechnol. Dec. 2010;5(12):868-73. doi: 10.1038/nnano.2010.213. Epub Nov. 14, 2010.
International Preliminary Report on Patentability dated Jun. 25, 2013 for PCT Application No. JP2013/059645.
International search report and written opinion dated Jan. 26, 2015 for PCT Application No. US2014/060742.
International Search Report and Written Opinion dated Feb. 17, 2015 for PCT Application No. IB2014/002143.
International search report and written opinion dated May 19, 2015 for PCT/JP2015/054796.
International search report and written opinion dated Jun. 24, 2015 for PCT/JP2015/052601.
International Search Report and Written Opinion dated Jun. 25, 2013 for PCT Application No. JP2013/059645.
International search report and written opinion dated Aug. 11, 2015 for PCT/JP2015/063403.
International search report and written opinion dated Aug. 18, 2015 for PCT/JP2015/063963.
International search report and written opinion dated Aug. 18, 2015 for PCT/JP2015/063964.
International search report and written opinion dated Aug. 18, 2015 for PCT/JP2015/063965.
International search report and written opinion dated Oct. 29, 2013 for PCT Application No. JP2013/071059.
International search report and written opinion dated Dec. 19, 2014 for PCT Application No. US2014/056173.
International Search Report and Written Opinion dated Dec. 6, 2016 for International Application No. PCT/JP2016/004531.
International Search Report and Written Opinion dated Feb. 24, 2015 for PCT Application No. IB2014/002128.
Ivanov, et al. DNA tunneling detector embedded in a nanopore. Nano Lett. Jan. 12, 2011;11(1):279-85. doi: 10.1021/nl103873a. Epub Dec. 6, 2010.
Kaji, et al. Separation of long DNA molecules by quartz nanopillar chips under a direct current electric field. Anal. Chem., Jan. 1, 2004, 76(1): pp. 15-22.
Keyser, et al. Direct force measurements on DNA in a solid-state nanopore. Nature Physics, vol. 2, Jul. 2006, pp. 473-477.
Lagerqvist, et al. "Fast DNA Sequencing via Transverse Electronic Transport", American Chemical Society, Nano Letters, 2006, vol. 6, No. 4, pp. 779-782.
Lagerqvist, et al. Influence of the Environment and Probes on Rapid DNA Sequencing via Transverse Electronic Transport. Biophysical Journel, vol. 93, Oct. 2007, pp. 2384-2390.
Lee, et al. Surface charge study on pollen with a simple microelectrophoresis instrumentation setup. Biomedical Engineering and Sciences (IECBES), 2010 IEEE EMBS Conference on. Kuala Lumpur, Malaysia, Nov. 30-Oct. 2, 2010, pp. 364-368.
Lesser-Rojas, et al. Tandem array of nanoelectronic readers embedded coplanar to a fluidic nanochannel for correlated single biopolymer analysis. Biomicrofluidics. Jan. 10, 2014;8(1):016501. doi: 10.1063/1.4861435. eCollection 2014. With Supplementary Materials.
Li, et al. Ion-beam sculpting at nanometer length scales. Nature, vol. 412, Jul. 2001, pp. 166-169.
Liang, et al. Nanogap Detector Inside nanofluidic Channel for Fast Real-Time Label-Free DNA Analysis. American Chemical Society, Nano Letters 2008, vol. 8, No. 5, pp. 1472-1476.
Maleki, et al. A nanofluidic channel with embedded transverse nanoelectrodes. Nanotechnology, 20, (2009) 105302, pp. 1-6.
Mastrangelo, et al. The potential and challenges of nanopore sequencing. Nature Biotechnology. 26 (2008): 1146-1153.
Nadasan, et al. Design and fabrication of the microchannels for microfluidics applications. U.P.B. Sci. Bull., Series C, 2009, 71(4): pp. 125-34.

(56) References Cited

OTHER PUBLICATIONS

Nam, et al. Ionic field effect transistors with sub-10 nm multiple nanopores. Nano Lett. May 2009;9(5):2044-8. doi: 10.1021/nl900309s.
Notice of allowance dated Jul. 17, 2015 for U.S. Appl. No. 13/992,328.
Notice of allowance dated Jul. 21, 2016 for U.S. Appl. No. 13/975,610.
Notice of allowance dated Sep. 15, 2016 for U.S. Appl. No. 14/421,809.
Notice of allowance dated Oct. 8, 2015 for U.S. Appl. No. 13/992,328.
Notice of Allowance dated Dec. 6, 2016 for U.S. Appl. No. 15/061,871.
Office action dated Feb. 5, 2016 for U.S. Appl. No. 14/112,189.
Office action dated Feb. 19, 2016 for U.S. Appl. No. 13/975,610.
Office action dated Apr. 17, 2015 for U.S. Appl. No. 13/992,328.
Office action dated May 25, 2016 for U.S. Appl. No. 14/421,809.
Office action dated Jun. 23, 2016 for U.S. Appl. No. 14/111,352.
Office action dated Aug. 1, 2016 for U.S. Appl. No. 14/112,189.
Office action dated Aug. 26, 2016 for U.S. Appl. No. 14/687,856.
Office action dated Sep. 1, 2015 for U.S. Appl. No. 14/112,189.
Office action dated Sep. 9, 2016 for U.S. Appl. No. 15/061,871.
Office action dated Oct. 6, 2016 for U.S. Appl. No. 14/883,494.
Office Action dated Jan. 27, 2017 for U.S. Appl. No. 14/111,352.
Ohshiro, et al. Single-molecule electrical random resequencing of DNA and RNA. Scientific Reports 2, Article No. 501 (Jul. 10, 2012) doi:10.1038/srep00501.
Ohshiro et al. Supplementary Information for Single-Molecule Electrical Random Resequencing of DNA and RNA. Scientific Reports 2, Article No. 501 (Jul. 10, 2012). 23 pages. doi:10.1038/srep00501.
Oshiro, et al. Detection of post-translational modifications in single peptides using electron tunnelling currents. Nature Nanotechnology, vol. 9, pp. 835-840 (e-pub. Sep. 14, 2014).
Oshiro, et al. Single-molecule electrical random resequencing of DNA and RNA. Scientific Reports, vol. 2, Article No. 501 (internal pp. 1-7) (e-pub. Jul. 10, 2012) See abstract: p. 2; figures 1-4; and tables 1-3.
PCT/US2014/060742 International Preliminary Report on Patentability dated Apr. 19, 2016.
Pedone, et al. Data Analysis of Translocation Events in Nanopore Experiments. American Chemical Society, Anal. Chem. 2009, 81, pp. 9689.
Peng, et al. Reverse DNA translocation through a solid-state nanopore by magnetic tweezers. Nanotechnology. May 6, 2009;20(18):185101. doi: 10.1088/0957-4484/20/18/185101. Epub Apr. 14, 2009.
TW103135904 Search Report dated Dec. 6, 2018 (w/ English translation).
Qiu, et al. Detecting ssDNA at single-nucleotide resolution by sub-2-nanometer pore in monoatomic graphene: A molecular dynamics study. Applied Physics Letters 100.8 (2012): 083106. 4 pages.
Rothberg, et al. An integrated semiconductor device enabling non-optical genome sequencing. Nature. 475 (2011): 348-352.
Ruitenbeek, et al. Adjustable nanofabricated atomic size contacts. Rev. Sci. Instrum. 67, 108 (1996).
Schreiber et al. "Error rates for nanopore discrimination among cytosine, methylcytosine, and hydroxymethylcytosine along individual DNA strands" PNAS, 2013; 11 0(47): 18910-18915, p. 18910, col. 2, para 3.
Simmons, et al. Generalized Formula for the Electric tuneele Effect between Similar Electrodes Separated by a Thin Insulating Film. J. Appl. Phys. 34, 1793 (1963).
Smith, et al. Electrophoretic distributions of human peripheral blood mononuclear white cells from normal subjects and from patients with acute lymphocytic leukemia. Proc Natl Acad Sci U S A. Jul. 1976;73(7):2388-91.
Tsutsui et al. Electrical Detection of Single-Methylcytosines in a DNA Oligomer. J Am Chem Soc 133(23): 9124-9128 (May 11, 2011). DOI: 10.1021/ja203839e.
Stijin Van Dorp, et al. Origin of the electrophoretic force on DNA in solid-state nanopores. Nature Physics, vol. 5, May 2009, pp. 347-351.
Stoddart, et al. Single-nucleotide discrimination in immobolized DNA oligonucleotides with a biological nanopore. PNAS, May 12, 2009, vol. 106, No. 19, pp. 7702-7707.
Storm, et al. Fabrication of solid-state nanopores with single-nanometere precision. Nature Materials, vol. 2, Aug. 2003, pp. 537-540.
Suga et al. Influence of electrode size on resistance switching effect in nanogap junctions, Applied Physics Letter, 2010, 97(7):73118, 4 pages. Epub Aug. 20, 2010.
Taniguchi, et al. Denryu de Ichi Enki Bunshi o Shikibetsu suru. Chemistry, 2011, vol. 66, No. 8, pp. 42-46.
Taniguchi, et al. Development of Single-Molecule Bio-Nanodevices for Medical Applications. The Imaging Society of Japan, Feb. 10, 2013, vol. 52, No. 1, pp. 51-60.
Taniguchi, M. Ichibunshi Kaiseki Gijutsu ni yoru Jijisedai DNA Sequencer no Kaihatsu. Dai 69 Kai Hyomen Kagaku Kenkyukai Yoshishu. Mar. 9, 2011, pp. 23-26.
Trepagnier, et al. Controlling DNA Capture and Progagation through Artificial Nanopores. American Chemical Society, Nano Letters, 2007, vol. 7, No. 9, pp. 2824-2830.
Troisi, et al. Molecular signatures in the transport properties of molecular wire junctions: what makes a junction "molecular"? Small. Feb. 2006;2(2):172-81.
Tsutsui, et al. Fabrication of 0.5 nm electrode gaps using self-breaking technique. Applied Physics Letters 93, 163115 (2008); DOI: 10.1063/1.3006063.
Tsutsui, et al. Formation and self-breaking mechanism of stable atom-sized junctions. Nano Lett. Jan. 2008;8(1):345-9. Epub Dec. 21, 2007.
Tsutsui, et al., Formation and self-breaking mechanism of stable atom-sized junctions, Nano Letters, 2008, 8(1):345-349.
Tsutsui, et al. Identifying single nucleotides by tunnelling current. Nature Nanotechnology, Letters, Published Online: Mar. 21, 2010; DOI: 10.1038/NNANO.2010.42, pp. 1-5.
Tsutsui et al. Supplementary Information for Identifying Single Nucleotides by Tunneling Current. Nature Nanotechnology 5:286-290 (Mar. 21, 2010). doi: 10.1038/NNANO.2010.42.
Tsutsui et al. Supporting Information for Electrical Detection of Single-Methylcytosines in a DNA Oligomer. J Am Chem Soc 133(23): 9124-9128 (May 11, 2011). DOI: 10.1021/ja203839e.
Tsutsui, et al. Transverse electric field dragging of DNA in a nanochannel. Sci Rep. 2012;2:394. doi: 10.1038/srep00394. Epub May 3, 2012. 7 pages.
Tsutsui, et al. Transverse Field Effects on DNA-Sized Particle Dynamics. American Chemical Society, Nano Letters, 2009, vol. 9, No. 4, pp. 1659-1662.
Venkatesan, et al. Nanopore sensors for nucleic acid analysis. Nat Nanotechnol. Sep. 18, 2011;6(10):615-24. doi: 10.1038/nnano.2011.129.
Wang, et al. Mechanism of electron conduction in self-assembled alkanethiol monolayer devices. Phys. Rev. B 68, 035416—Published Jul. 17, 2003.
Woolley, et al. Capillary electrophoresis chips with integrated electrochemical detection.. Analytical Chemistry 70.4 (1998): 684-688.
Yen, et al. Gate effects on DNA translocation through silicon dioxide nanopore. Rev Sci Instrum. Mar. 2012;83(3):034301. doi: 10.1063/1.3692746.
Zhao, et al. Single-strand DNA molecule translocation through nanoelectrode gaps. Nanotechnology. Oct. 24, 2007;18(42):424018. doi: 10.1088/0957-4484/18/42/424018. Epub Sep. 19, 2007. 7 pages.
Zhou, et al. Microfabrication of a mechanically controllable break junction in silicon. Appl. Phys. Lett. 67, 1160 (1995).
Zwolak, et al. Colloquium: Physical approaches to DNA sequencing and detection. Reviews of Modern Physics, vol. 80, Jan.-Mar. 2008, pp. 141-165.
Zwolak, et al. Electronic Signature of DNA Nucleotides via Transverse Transport. American Chemical Society, Nano Letters, 2005, vol. 5, No. 3, pp. 421-424.

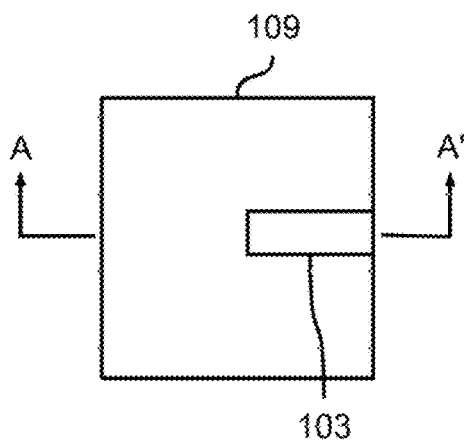
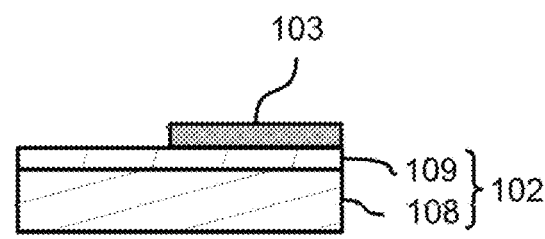
Fig. 13A          Fig. 13B
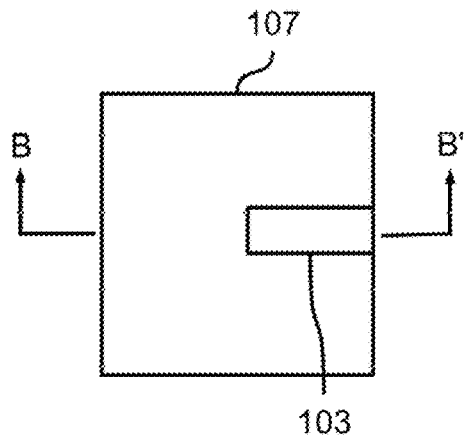
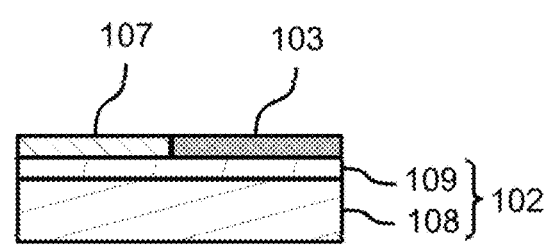
Fig. 13C          Fig. 13D
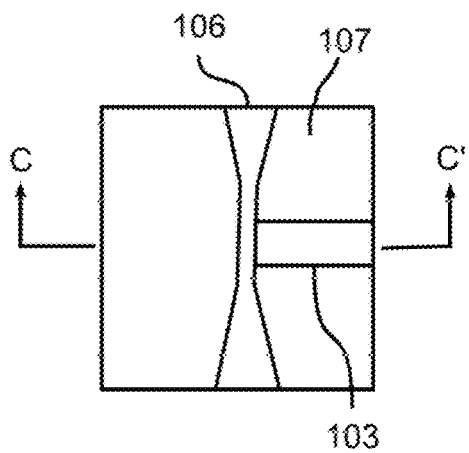
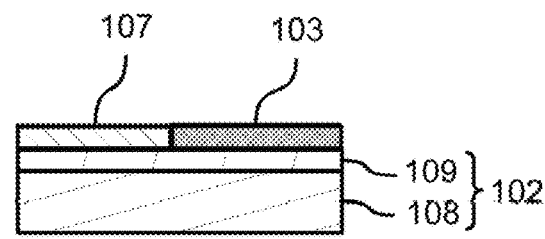
Fig. 13E          Fig. 13F

NANO-GAP ELECTRODE PAIR AND METHOD OF MANUFACTURING SAME

CROSS-REFERENCE

This application is a continuation of U.S. patent application Ser. No. 15/098,147, filed Apr. 13, 2016, which is a continuation of International Patent Application No. PCT/US2014/060742, filed Oct. 15, 2014, which claims priority to Japanese Patent Application Serial No. JP 2013-215828, filed Oct. 16, 2013, each of which is entirely incorporated herein by reference.

BACKGROUND

The present invention relates to a nano-gap electrode pair and a method of manufacturing a nano-gap electrode pair. In recent years, an electrode structure (hereinafter referred to as the nano-gap electrode pair) in which a nanoscale gap is formed between opposed electrode parts or formed G0 tips has been a focus of attention. Accordingly, studies are being made actively on electronic devices, biodevices and the like using nano-gap electrode pairs. For example, an analytical apparatus for analyzing the nucleotide sequence of DNA or RNA utilizing a nano-gap electrode pairs has been conceived of in the field of biodevices (see, for example, International Publication No. WO 2011/108540, which is entirely incorporated herein by reference).

In this analytical apparatus, a single DNA or RNA strand is passed through a nanoscale hollow gap (hereinafter referred to as a nano-gap) between electrode parts of a nano-gap electrode pair. Typically single stranded DNA or RNA may be used. Then, currents flowing through electrode parts when bases of a single DNA or RNA strand pass through the nano-gap between the electrode parts are measured, thereby enabling the bases constituting the DNA or RNA strand to be determined on the basis of the values of the currents.

In such an analytical apparatus as mentioned above, the detectable value of a current decreases if the distance between the electrode parts of the nano-gap electrode pair increases. This makes it difficult to analyze samples with high sensitivity. Accordingly, it is desired that the nano-gap between the electrode parts can be formed to be small in size. Accordingly, efforts are being made to develop a nano-gap electrode pair, the distance of which between the electrode parts is short (see, for example, Japanese Patent Laid-Open No. 2006-234799, which is entirely incorporated herein by reference).

Japanese Patent Laid-Open No. 2006-234799, which is entirely incorporated herein by reference, discloses a method for manufacturing a vertical nano-gap on a substrate by creating a three-layer structure comprising a metal layer, a self-assembled monolayer (SAM) or $Al_2O_3$ layer, and a metal layer, and then removing the SAM or $Al_2O_3$ layer. Japanese Patent Laid-Open No. 2006-234799, which is entirely incorporated herein by reference, also discloses a method for creating a planar nano-gap between a first metal layer and a second metal layer by forming an SAM on a side surface of the first metal layer disposed on a substrate as one electrode part, forming the second metal layer to serve as the other electrode part on the substrate, so as to have contact with the SAM, and then removing the SAM.

Although the distance between the electrode parts can be narrowed in the nano-gap electrode, in some cases, the narrowed distance between the electrode parts may make it more difficult for a single stranded DNA-containing sample solution measurement target to pass through the nano-gap.

Hence, an object of the present invention, which has been accomplished in view of the above-described problem, is to propose a nano-gap electrode pair and a method for manufacturing a nano-gap electrode pair in which a sample fluid can easily pass through a nano-gap between a first electrode part and a second electrode part even if the width of the nano-gap is made to be substantially narrow.

SUMMARY

The present disclosure provides nano-gap electrode devices and systems. Nano-gap electrode devices and systems provided herein may be capable of solving at least some of the problems described above.

A nano-gap electrode pair may in some embodiments include a first electrode part formed on a substrate; a second electrode part formed on either a gap-forming layer formed above a first electrode part on an insulating layer or a gap-forming layer formed on the first electrode part and disposed oppositely to the first electrode part; and a nano-gap formed between the first electrode part and the second electrode part, the nano-gap being composed of a first nano-gap region coplanar to a substrate, and a second nano-gap region extending perpendicularly to the substrate, the terminal end of the second nano-gap region connecting or overlapping first nano-gap region.

A nano-gap electrode pair may in some embodiments include a first electrode part formed on a substrate; a second electrode part formed on a gap-forming layer on the substrate and disposed oppositely to the first electrode part; and a nano-gap formed between the first electrode part and the second electrode part, the nano-gap comprising a first nano-gap region coplanar to a substrate and a second nano-gap region extending perpendicularly to the substrate, the terminal end of the second nano-gap region connecting or overlapping with the first nano-gap region.

In an aspect of the present disclosure, a nano-gap electrode pair comprises a first electrode part formed on a substrate; a second electrode part formed on either a gap-forming layer formed in the first electrode part through an insulating layer or a gap-forming layer formed in the first electrode part and disposed oppositely to the first electrode part; and a nano-gap formed between the first electrode part and the second electrode part, the nano-gap being composed of a first gap region extending in a planar direction of the substrate and a second gap region extending perpendicularly to the substrate, the terminal end of the second gap region being connected with the first gap region. In an embodiment, the first electrode part includes: a thin-film part; a thick-film part thicker in film thickness than the thin-film part; and a first electrode-side gap-forming part formed between the thin-film part and the thick-film part and thinner in film thickness than the thick-film part. The second electrode part can include: a base part disposed on the thin-film part through the insulating layer and the gap-forming layer or through the gap-forming layer only; and a second electrode-side gap-forming part the leading end of which extends from the base part toward the thick-film part, thereby forming the first gap region between the first electrode-side gap-forming part and the second electrode-side gap-forming part and the second gap region between the thick-film part and the second electrode-side gap-forming part.

In another aspect, a nano-gap electrode pair comprises a first electrode part formed on a substrate; a second electrode part formed in a gap-forming layer on the substrate and disposed oppositely to the first electrode part; and a nano-gap formed between the first electrode part and the second electrode part, the nano-gap being composed of a first gap region extending in a planar direction of the substrate and a second gap region extending perpendicularly to the substrate, the terminal end of the second gap region being connected with the first gap region. In an embodiment, the second electrode part includes: a base part disposed on the substrate through the gap-forming layer; and a second electrode-side gap-forming part formed so as to run upon the first electrode part with the first gap region and the second gap region provided between the first electrode part and the second electrode-side gap-forming part.

In an embodiment, the width of the first gap region and the width of the second gap region are the same in dimensions as the film thickness of the gap-forming layer.

In another aspect, a system for detecting a biomolecule comprises a nano-gap electrode device including a first electrode and a second electrode adjacent to the first electrode, wherein the first electrode is separated from the second electrode by a nano-gap that is dimensioned to permit the biomolecule to flow through the nano-gap, wherein the nano-gap has at least a first gap region and a second gap region, wherein the second gap region is oriented at an angle that is greater than zero degrees with respect to a plane having or defining the first gap region; and an electrical circuit coupled to the nano-gap electrode device, wherein the electrical circuit receives electrical signals from the first electrode and the second electrode upon the flow of the biomolecule through the nano-gap.

In some embodiments, the second gap region is oriented at an angle that is greater than about 25° with respect to the plane having or defining the first gap region. In some embodiments, the second gap region is oriented at an angle that is greater than about 45° with respect to the plane having or defining the first gap region. In some embodiments, the second gap region is oriented at an angle that is about 90° with respect to the plane having or defining the first gap region.

In some embodiments, the first electrode is adjacent to a substrate. In some embodiments, the second electrode is adjacent to an insulating layer that is in contact with the first electrode. In some embodiments, the first electrode comprises a first portion and a second portion that is adjacent to the first portion, wherein the first and second portions are adjacent to the substrate, and wherein the first portion has a greater thickness than the second portion. In some embodiments, the first portion has a surface that partially defines the second gap region, and wherein the second portion has a surface that partially defines the first gap region.

In some embodiments, a portion of the first electrode or the second electrode has a single atom tip. In some embodiments, a terminal end of the second gap region is coupled to the first gap region. In some embodiments, the system further comprises at least one channel in fluid communication with the nano-gap electrode device and configured to direct the biomolecule to the nano-gap. In some embodiments, the channel is integrated with a microfluidic structure.

In some embodiments, the electrical circuit is part of or in communication with a computer processor that is programmed to detect the biomolecule or portion thereof from the electrical signals. In some embodiments, the nano-gap electrode device is part of an array of nano-gap electrode devices. In some embodiments, the nano-gap electrode device is independently addressable with respect to other nano-gap electrode devices of the array.

In some embodiments, the nano-gap has a third gap region, a terminal end of which is coupled to the first gap region.

In another aspect, a system for sensing a biomolecule comprises a nano-gap electrode device including a first electrode and a second electrode adjacent to the first electrode, wherein the first electrode is separated from the second electrode by a nano-gap that is dimensioned to permit the biomolecule to flow through the nano-gap, wherein the nano-gap has a first gap region and a second gap region, wherein the second gap region is oriented at an angle that is about 90° degrees with respect to a plane having or defining the first gap region, and wherein a terminal end of the second gap region is coupled to the first gap region.

In some embodiments, the first electrode is adjacent to a substrate. In some embodiments, the second electrode is adjacent to an insulating layer that is in contact with the first electrode. In some embodiments, the first electrode comprises a first portion and a second portion that is adjacent to the first portion, wherein the first and second portions are adjacent to the substrate, and wherein the first portion has a greater thickness than the second portion. In some embodiments, the first portion has a surface that partially defines the second gap region, and wherein the second portion has a surface that partially defines the first gap region.

In some embodiments, a portion of the first electrode or the second electrode has a single atom tip. In some embodiments, the system further comprises at least one channel in fluid communication with the nano-gap electrode device and configured to direct the biomolecule to the nano-gap. In some embodiments, the channel is integrated with a microfluidic structure.

In some embodiments, the nano-gap electrode device is part of an array of nano-gap electrodes. In some embodiments, the nano-gap electrode device is independently addressable with respect to other nano-gap electrode devices of the array.

In some embodiment, the nano-gap has a third gap region, a terminal end of which is coupled to the first gap region.

The present disclosure also provides a method for detecting a biomolecule, comprising using any of the devices or systems described above or elsewhere herein to detect the biomolecule.

In an aspect, a method for detecting a biomolecule comprises: (a) directing a biomolecule to a nano-gap electrode device having a first electrode and a second electrode adjacent to the first electrode, wherein the first electrode is separated from the second electrode by a nano-gap that is dimensioned to permit the biomolecule to flow through the nano-gap, wherein the nano-gap has at least a first gap region and a second gap region, and wherein the second gap region is oriented at an angle that is greater than zero degrees with respect to a plane having or defining the first gap region; (b) measuring electrical signals upon the flow of the biomolecule through the nano-gap; and (c) detecting the biomolecule using the electrical signals measured in (b).

In some embodiments, the detecting comprises comparing the electrical signals to reference signals that are indicative of the biomolecule or a portion thereof. In some embodiments, the detecting comprises identifying the biomolecule or a portion thereof. In some embodiments, the biomolecule is a nucleic acid molecule. In some embodiments, the detecting in (c) comprises sequencing the nucleic acid molecule.

In some embodiments, the electrical signals include electrical current. In some embodiments, the electrical current is tunneling current.

In some embodiments, the second gap region is oriented at an angle that is about 90° with respect to the plane having or defining the first gap region. In some embodiments, a portion of the first electrode or the second electrode has a single atom tip. In some embodiments, the biomolecule is directed to the nano-gap electrode device through at least one channel that is in fluid communication with the nano-gap electrode device. In some embodiments, the nano-gap electrode device is part of an array of independently addressable nano-gap electrode devices. In some embodiments, upon the flow of the biomolecule through the nano-gap, a portion of the biomolecule flows through the first gap region and a remainder of the biomolecule flows through the second gap region.

The present disclosure also provides methods for manufacturing any of the devices and systems described above or elsewhere herein.

In an aspect, a method for manufacturing nano-gap electrodes for use in detecting a biomolecule, comprises: (a) providing a first electrode-forming part adjacent to a substrate; (b) forming a gap-forming layer adjacent to a surface of the first electrode-forming part; (c) forming a second electrode-forming part adjacent to the gap-forming layer; and (d) removing a portion of the gap-forming layer to form a nano-gap between the first electrode part and the second electrode part, wherein the nano-gap is dimensioned to permit the biomolecule to flow through the nano-gap, wherein the nano-gap has at least a first gap region and a second gap region, and wherein the second gap region is oriented at an angle that is greater than zero degrees with respect to a plane having or defining the first gap region.

In some embodiments, the method further comprises, subsequent to (c), exposing a surface of the first electrode-forming part, a surface of the second portion of the gap-forming layer, and a surface of the second electrode-forming part. In some embodiments, the method further comprises patterning the second electrode-forming part, the gap-forming layer and the first electrode-forming part to provide a first electrode part and a second electrode part each having a predetermined shape.

In some embodiments, the second gap region is oriented at an angle that is greater than about 25° with respect to the plane having or defining the first gap region. In some embodiments, the second gap region is oriented at an angle that is greater than about 45° with respect to the plane having or defining the first gap region. In some embodiments, the second gap region is oriented at an angle that is about 90° with respect to the plane having or defining the first gap region.

In some embodiments, the method further comprises processing the first electrode part and/or the second electrode part to have a single atom tip. In some embodiments, the first electrode part and the second electrode part are processed to each have a single atom tip. In some embodiments, the method further comprises providing at least one channel in fluid communication with the nano-gap. In some embodiments, step (a) of the method comprises forming an insulating layer adjacent to a portion of the electrode-forming part having a lower thickness than another portion of the electrode-forming part, and forming the gap-forming layer adjacent to the insulating layer. In some embodiments, a terminal end of the second gap region is coupled to the first gap region. In some embodiments, the first electrode-forming part has a level difference. In some embodiments, the first gap region is parallel to the substrate.

In another aspect, a method of manufacturing a nano-gap electrode pair includes a first operation of forming a first electrode-forming part having multiple different levels on a substrate, and then forming a gap-forming layer along a lower level of the first electrode-forming part, thereby forming the gap-forming layer coplanar to a substrate and perpendicularly to the substrate; a second operation of forming a second electrode-forming part on the gap-forming layer, and then exposing a surface of the first electrode-forming part, a surface of the gap-forming layer extending perpendicularly to the substrate, and a surface of the second electrode-forming part; a third operation of patterning the second electrode-forming part, the gap-forming layer and the first electrode-forming part using a mask, thereby forming a first electrode part and a second electrode part each having a predetermined shape, and forming the gap-forming layer coplanar to a substrate and perpendicularly to the substrate between the first electrode part and the second electrode part; and a fourth operation of removing the gap-forming layer, thereby forming a nano-gap comprising a first nano-gap region coplanar to a substrate and a second nano-gap region extending perpendicularly to the substrate, the terminal end of the second nano-gap region connecting or overlapping with the first nano-gap region, between the first electrode part and the second electrode part.

In another aspect, a method of manufacturing a nano-gap electrode pair includes a first operation of forming a first electrode-forming part on a substrate, and then forming a gap-forming layer on the first electrode-forming part and the substrate, thereby forming the gap-forming layer coplanar to the substrate and perpendicularly to the substrate; a second operation of forming a second electrode-forming part on the gap-forming layer; a third operation of patterning the second electrode-forming part, the gap-forming layer and the first electrode-forming part using a mask, thereby forming a first electrode part and a second electrode part each having a predetermined shape, and forming the gap-forming layer coplanar to the substrate and perpendicularly to the substrate between the first electrode part and the second electrode part; and a fourth operation of removing the gap-forming layer, thereby forming a nano-gap composed of a first nano-gap region coplanar to the substrate and a second nano-gap region extending perpendicularly to the substrate, the terminal end of the second nano-gap region connecting or overlapping with the first gap region, between the first electrode part and the second electrode part.

In another aspect, a method of manufacturing a nano-gap electrode pair comprises forming a first electrode-forming part having a level difference on a substrate, and then forming a gap-forming layer along the level difference of the first electrode-forming part, thereby forming the gap-forming layer extending in a planar direction of the substrate and perpendicularly to the substrate; forming a second electrode-forming part on the gap-forming layer, and then exposing a surface of the first electrode-forming part, a surface of the gap-forming layer extending perpendicularly to the substrate, and a surface of the second electrode-forming part; patterning the second electrode-forming part, the gap-forming layer and the first electrode-forming part using a mask, thereby forming a first electrode part and a second electrode part each having a predetermined shape, and forming the gap-forming layer extending in the planar direction of the substrate and perpendicularly to the substrate between the first electrode part and the second electrode part; and removing the gap-forming layer, thereby forming a nano-gap composed of a first gap region extending in the planar direction of the substrate and a second gap region extending perpendicularly to the substrate, the terminal end of the second gap region being connected with the first gap region, between the first electrode part and the second electrode part. In an embodiment, forming the first electrode-forming part comprises forming an insulating layer in a region thin in film thickness on the first electrode-forming part having the level difference, and then forming the gap-forming layer along the level difference of the first electrode-forming part and the insulating layer, and the patterning comprises patterning the insulating layer as well using the mask to dispose the insulating layer in a region of the first electrode part thin in film thickness.

In another aspect, a method of manufacturing a nano-gap electrode pair comprises forming a first electrode-forming part on part of a substrate, and then forming a gap-forming layer on the first electrode-forming part and the substrate, thereby forming the gap-forming layer extending in a planar direction of the substrate and perpendicularly to the substrate; forming a second electrode-forming part on the gap-forming layer; patterning the second electrode-forming part, the gap-forming layer and the first electrode-forming part using a mask, thereby forming a first electrode part and a second electrode part each having a predetermined shape, and forming the gap-forming layer extending in the planar direction of the substrate and perpendicularly to the substrate between the first electrode part and the second electrode part; and removing the gap-forming layer, thereby forming a nano-gap composed of a first gap region extending in the planar direction of the substrate and a second gap region extending perpendicularly to the substrate, the terminal end of the second gap region being connected or overlapping with the first gap region, between the first electrode part and the second electrode part.

According to various embodiments, it is possible to form a nano-gap electrode pair in which a sample fluid can pass through not only the first nano-gap region coplanar to the substrate but also the second nano-gap region extending perpendicularly to the substrate, the terminal end of the second nano-gap region connecting or overlapping with the first nano-gap region, the nano-gap between the first electrode part and the second electrode part is selected to have a small width, sample fluid can easily pass through the nano-gap.

In some embodiments nanochannels may be constructed in association with one or more nano-gap electrode pairs so as to control the flow of a sample, which may be DNA such that a higher percentage of the sample may interact with the nanogap electrode pairs.

In other embodiments, stable Go tips may be formed associated with the nano-gap electrode pairs so as to better and more reliably and precisely measure a sample.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 13A-13F are schematic views of a method for manufacturing the nano-gap electrode chip of FIG. 11A;

DETAILED DESCRIPTION

Figure 1:
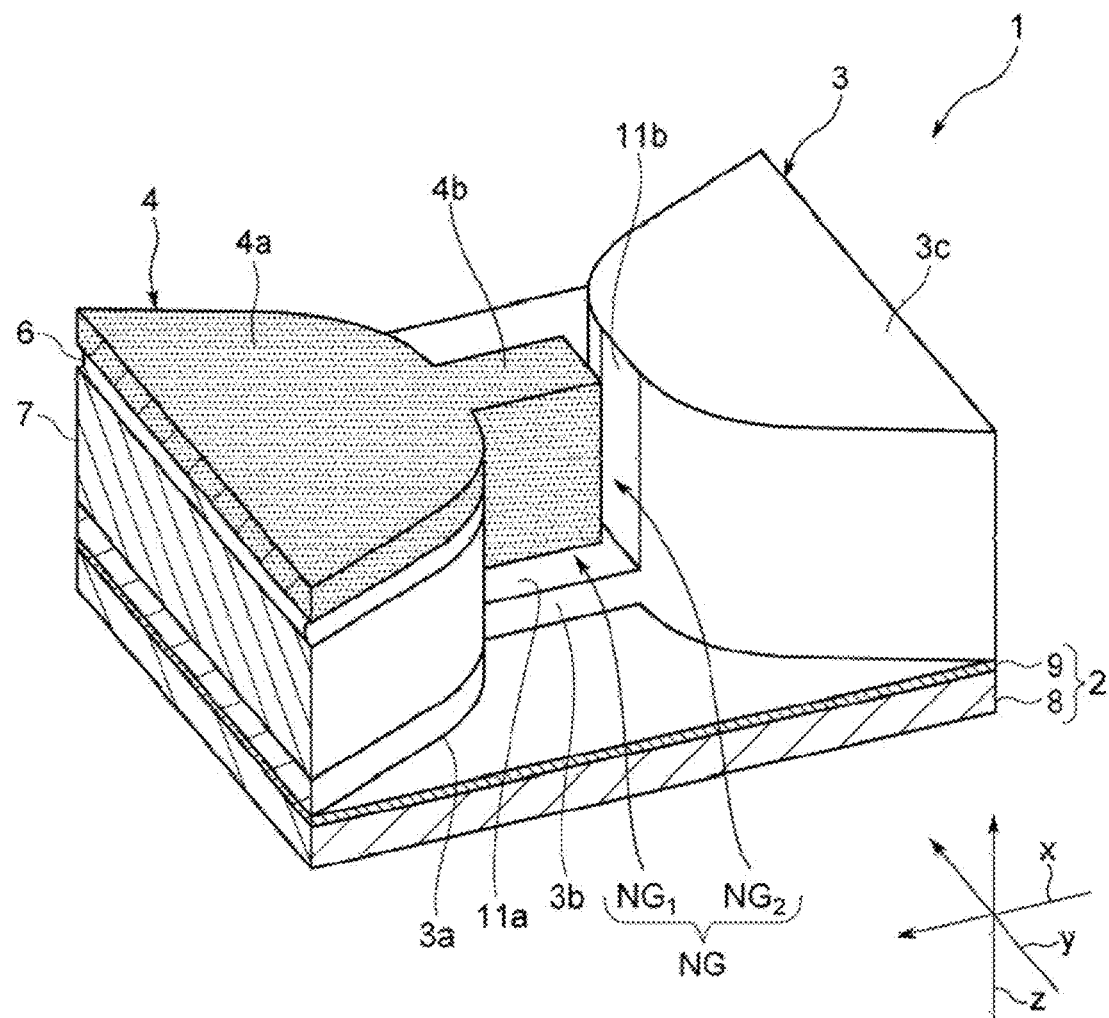
FIG. 1 is a schematic view illustrating the overall configuration of a nano-gap electrode pair.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "gap," as used herein, generally refers to a pore, channel or passage formed or otherwise provided in a material. The material may be a solid state material, such as a substrate. The gap may be disposed adjacent or in proximity to a sensing circuit or an electrode coupled to a sensing circuit. In some examples, a gap has a characteristic width or diameter on the order of 0.1 nanometers (nm) to about 1000 nm. A gap having a width on the order of nanometers may be referred to as a "nano-gap" (also "nanogap" herein). In some situations, a nano-gap has a width that is from about 0.1 nanometers (nm) to 50 nm, 0.5 nm to 30 nm, or 0.5 nm or 10 nm, 0.5 nm to 5 nm, or 0.5 nm to 2 nm, or no greater than 2 nm, 1 nm, 0.9 nm, 0.8 nm, 0.7 nm, 0.6 nm, or 0.5 nm. In some cases, a nano-gap has a width that is at least about 0.5 nm, 0.6 nm, 0.7 nm, 0.8 nm, 0.9 nm, 1 nm, 2 nm, 3 nm, 4 nm, or 5 nm. In some cases, the width of a nano-gap can be less than a diameter of a biomolecule or a subunit (e.g., monomer) of the biomolecule.

The term "electrode," as used herein, generally refers to a material or part that can be used to measure electrical current. An electrode (or electrode part) can be used to measure electrical current to or from another electrode. In some situations, electrodes can be disposed in a channel (e.g., nanogap) and be used to measure the current across the channel. The current can be a tunneling current. Such a current can be detected upon the flow of a biomolecule (e.g., protein) through the nano-gap. In some cases, a sensing circuit coupled to electrodes provides an applied voltage across the electrodes to generate a current. As an alternative or in addition to, the electrodes can be used to measure and/or identify the electric conductance associated with a biomolecule (e.g., an amino acid subunit or monomer of a protein). In such a case, the tunneling current can be related to the electric conductance.

The term "biomolecule," as used herein generally refers to any biological material that can be interrogated with an electrical current and/or potential across a nano-gap electrode. A biomolecule can be a nucleic acid molecule, protein, or carbohydrate. A biomolecule can include one or more subunits, such as nucleotides or amino acids.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded.

The term "protein," as used herein, generally refers to a biological molecule, or macromolecule, having one or more amino acid monomers, subunits or residues. A protein containing 50 or fewer amino acids, for example, may be referred to as a "peptide." The amino acid monomers can be selected from any naturally occurring and/or synthesized amino acid monomer, such as, for example, 20, 21, or 22 naturally occurring amino acids. In some cases, 20 amino acids are encoded in the genetic code of a subject. Some proteins may include amino acids selected from about 500 naturally and non-naturally occurring amino acids. In some situations, a protein can include one or more amino acids selected from isoleucine, leucine, lysine, methionine, phenylalanine, threonine, tryptophan and valine, arginine, histidine, alanine, asparagine, aspartic acid, cysteine, glutamine, glutamic acid, glycine, proline, serin and tyrosine.

The term "level difference," as used herein generally refers to a part that has different dimensions along a given axis (e.g., z axis), in some cases different thicknesses. For example, a level difference can be a part that has a first thickness at one portion and a second thickness at a second portion, which first thickness and second thickness are different.

Nano-Tap Electrode Pairs and Methods

The present disclosure provides methods and systems that can be used to detect a biomolecule, such as DNA or RNA, including single-stranded DNA or RNA. In some cases, a biomolecule or portion (e.g., subunits) thereof is detected using a pair of electrodes in a nano-gap by measuring a current from one electrode to another when the biomolecule or portion thereof is situated in the nano-gap. The biomolecule can be flowing through the nano-gap while current measurements are made to detect the biomolecule or portion thereof (e.g., subunits of the biomolecule).

A nano-gap can be part of a nano-gap array having a plurality of nano-gaps. Each nano-gap can include a plurality of electrodes. The electrodes of each nano-gap (also "nano-gap electrodes" herein) can be independently addressable with respect to other nano-gap electrodes of the array.

The current can be a tunneling current. Such a current can be detected upon the flow of the biomolecule through the nano-gap. In some cases, a sensing circuit coupled to the electrodes provides an applied voltage across the electrodes to generate a current. As an alternative or in addition to, the electrodes can be used to measure and/or identify the electric conductance associated with the target species (e.g., a base of a nucleic acid molecule). In such a case, the tunneling current can be related to the electric conductance.

The present disclosure provides a nano-gap electrode pair in which a sample containing fluid (e.g., a biomolecule in a fluid medium) can readily pass through a nano-gap between a first electrode part and a second electrode part and associated nanochannel, even if the width of the nano-gap is made to be substantially small and G0 tips are formed as a part of the first and second electrode parts. In a nano-gap electrode pair, a solution can pass through not only a first gap region NG1 coplanar to a substrate but also a second gap region NG2 extending at an angle (e.g., perpendicularly) with respect to a plane having the substrate. The angle can be greater than about 0°, or at least about 1°, 2°, 3°, 4°, 5°, 6°, 7°, 8°, 9°, 10°, 15°, 20°, 25°, 30°, 35°, 40°, 45°, 50°, 60°, 70°, 80°, 90°, 100, 110°, 120°, 130°, or 135°. A terminal end of the second gap region NG2 can be connected to or overlapping with a first gap region NG1. In some cases, if a nano-gap NG between a first electrode part and a second electrode part is formed so as to have a small width W1, a solution containing the biomolecule (e.g., single stranded or double stranded DNA) can readily pass through the nano-gap NG.

In FIG. 1, reference numeral 1 denotes a nano-gap electrode pair, where a first electrode part 3 having a predetermined shape may be disposed on a substrate 2, a second electrode part 4 may be disposed on a thin-film part 3a provided in the first electrode part 3 wherein an insulating layer 7 and an insulating layer 6 may serve as a gap-forming layer(s), and first electrode part 3 and second electrode part 4 may form a hollow nano-gap NG the width of which is nanoscale (no greater than, for example, 1000 nm). In some embodiments, a nano-gap NG may be composed of a first gap region NG1 disposed parallel to substrate 2 and a second gap region NG2 disposed perpendicularly to substrate 2, the terminal end of second gap region NG2 being connected or overlapped with first gap region NG1, and extending in two directions may be formed between first electrode part 3 and second electrode part 4. Substrate 2 may be composed of, for example, a silicon substrate 8 and a layer-like silicon oxide layer 9 formed on silicon substrate 8, and may have a configuration in which first electrode part 3 may be made from a metal material, such as titanium nitride (TiN), is formed on silicon oxide layer 9.

The substrate 8 may be formed of a semiconductor, such as a Group IV semiconductor or a Group III-V semiconductor. Examples of semiconductor for use as the substrate 8 include silicon, germanium, and gallium arsenide.

In practice, in this embodiment, first electrode part 3 may be composed of thin-film part 3a on a surface on which insulating layer 7 and insulating layer 6 may be added; band shaped first electrode-side gap-forming part 3b, one end of which may be formed integrally with thin-film part 3a; and a thick-film part 3c formed integrally with the other end of first electrode-side gap-forming part 3b. First electrode part 3 may have a configuration in which thin-film part 3a and first electrode-side gap-forming part 3b may be formed so as to have a thinner film thickness than thick-film part 3c, and second electrode part 4 may be disposed above thin-film part 3a and first electrode-side gap-forming part 3b. Consequently, first electrode part 3 may be disposed so that second electrode part 4 may overlap with thin-film part 3a and part of first electrode-side gap-forming part 3b, may be formed so that second electrode part 4 does not overlap thick-film part 3c, which may have a greater film thickness, and therefore, the upper surface of the thick-film part 3c may be exposed.

While the band shaped, second electrode-side gap-forming part 4b is shown as a rectangular feature in the figures, this is not essential. Substantially small rectangular features with sharp corners are difficult to create using photolithographic methods. In some embodiments the electrode end can be rounded so a limited number of atoms provide the shortest distance of the nano-gap.

In some embodiments as illustrated in FIG. 1, first electrode part 3 may be formed such that the outer shapes of thin-film part 3a and thick-film part 3c may be substantially bilaterally symmetrical with respect to the band shaped first electrode-side gap-forming part 3b. In some embodiments first electrode part 3 may have a configuration in which, for example, the outer shape of thin-film part 3a may be formed into a substantially bulbous or tapering shape, the outer shape of thick-film part 3c may also be formed into a substantially bulbous or tapering shape, and the edges of band shaped first electrode-side gap-forming part 3b may be formed integrally with the respective central leading edges of thin-film part 3a and thick-film part 3c.

In some embodiments thick-film part 3c may be formed so as have a thicker film thickness than thin-film part 3a and first electrode-side gap-forming part 3b. Accordingly, a gap-forming side surface 11b having a height corresponding to a difference in the film thickness first electrode part 3 between a thickness of first electrode-side gap-forming part 3b and a thickness of thick-film part 3c. This first electrode part 3 may have a configuration in which thin-film part 3a and first electrode-side gap-forming part 3b may be formed so as to be the same in film thickness, such that first electrode part 3 has a difference in film thickness only between first electrode-side gap-forming part 3b and thick-film part 3c, wherein second electrode part 4 may be disposed above thin-film part 3a and first electrode-side gap-forming part 3b which may be formed so as to be flush with each other.

In other embodiments, first electrode-side gap-forming part 3b may have a planar gap-forming upper surface 11a disposed orthogonally to gap-forming side surface 11b of thick-film part 3c, and a second electrode-side gap-forming part 4b of second electrode part 4 may be disposed at least in part across from gap-forming upper surface 11a. Here, a configuration in which a base part 4a of second electrode part 4 may be disposed on insulating layers 6 and 7, and thin-film part 3a may be electrically isolated from the second electrode part 4 by insulating layers 6 and 7.

In some embodiments, insulating layer 6 may be formed from an insulating material, such as silicon nitride (SiN), which may etch differently in etching conditions from insulating layer 7 and silicon oxide layer 9. In other embodiments, insulating layer 6 may be formed on insulating layer 7, and insulating layer 6 may have an outer shape almost the same as the outer shape of thin-film part 3a of first electrode part 3, and may be formed along a side surface of insulating layer 7 in a predetermined region near the central leading edge of thin-film part 3a. The exposed surface of insulating layer 6 may be etched by a time limited wet etch performed at the time of nano-gap formation in the course of manufacture (described later), and therefore, insulating layer 6 may be formed to be slightly smaller in outer shape than thin-film part 3a. Also in this embodiment, insulating layer 7 may differ in etching conditions from insulating layer 6 and silicon oxide layer 9, and may be formed from an insulating material, such as alumina ($Al_2O_3$), capable of insulating first electrode part 3 and second electrode part 4 from each other. In addition, insulating layer 7 may have an outer shape almost the same as the outer shape of thin-film part 3a of first electrode part 3, and insulating layer 6 may be formed on the upper surface and part of the side surfaces of insulating layer 7.

Second electrode part 4 may be formed from a metal material, such as titanium nitride (TiN), and may include base part 4a formed on insulating layer 6 and band shaped narrow strip, second electrode-side gap-forming part 4b one end of which may be formed integrally with base part 4a. In some embodiments, base part 4a of second electrode part 4 may have the same outer shape as the outer shape of thin-film part 3a of first electrode part 3, and may be disposed on first electrode part 3, so that the outer circumference of base part 4a conforms to the outer circumference of thin-film part 3a of first electrode part 3. In addition, a film thickness of second electrode-side gap-forming part 4b may be selected to be thicker than a film thickness of base part 4a.

An X-axis length of second electrode-side gap-forming part 4b of second electrode part 4 extending in an x direction may be selected to be shorter than an X-axis length of first electrode-side gap-forming part 3b extending in the x direction at first electrode part 3. Consequently, although the outer circumference of second electrode-side gap-forming part 4b may be disposed so as to conform to the outer circumference of first electrode-side gap-forming part 3b, it is possible to form second gap region NG2 (nano-gap NG) having a width W1 and extending to the top of second electrode part 4, as illustrated in FIG. 2A which shows the top view of a nano-gap electrode pair of FIG. 1.

Figure 2A:
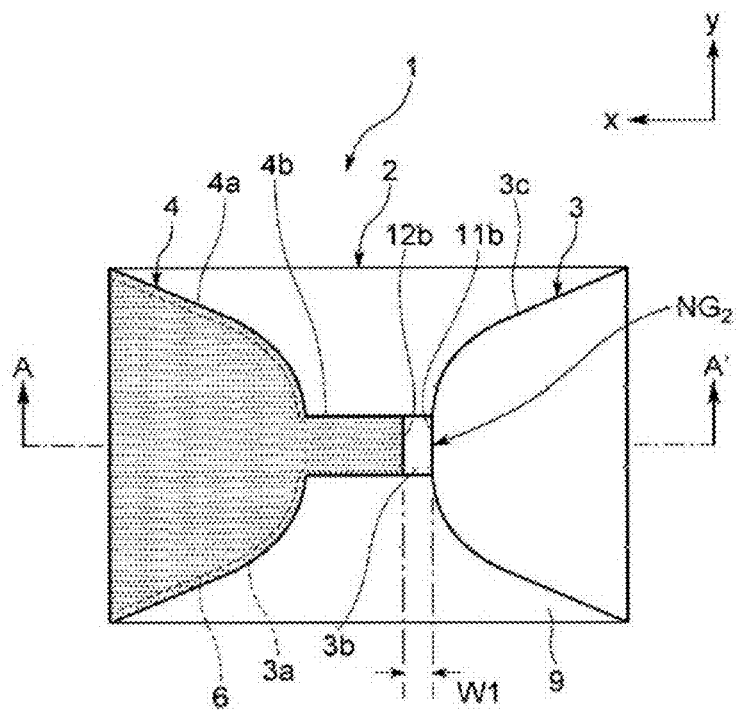
FIG. 2A is a top view illustrating an upper-surface configuration of a nano-gap electrode pair.
Figure 2B:
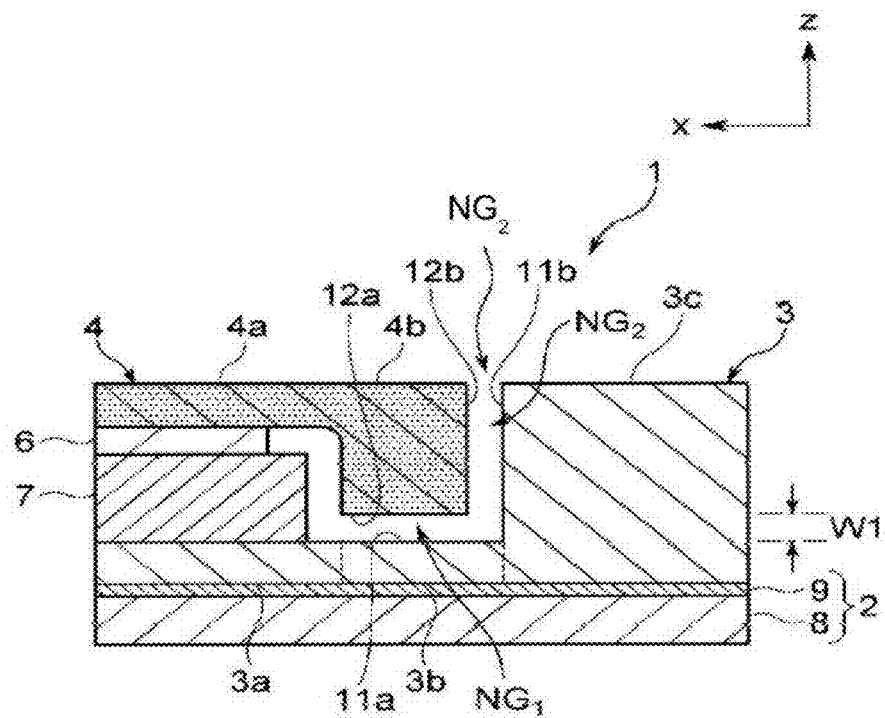
FIG. 2B is a cross-sectional side view illustrating a lateral cross-sectional configuration of a nano-gap electrode pair.

In some embodiments as illustrated in FIG. 2B which shows the lateral cross-sectional configuration of section A-A' in FIG. 2A, the bottom of second electrode-side gap-forming part 4b may be cantilever-supported by base part 4a, and the leading end of second electrode-side gap-forming part 4b may extend toward thick-film part 3c, thus forming first gap region NG1 (nano-gap NG) having a height W1 corresponding to the film thickness of insulating layer 6 between second electrode-side gap-forming part 4b and gap-forming upper surface 11a of first electrode-side gap-forming part 3b. In some embodiments, an opposed-to-gap lower surface 12a located on the bottom side of second electrode-side gap-forming part 4b may be disposed oppositely to gap-forming upper surface 11a of first electrode-side gap-forming part 3b, as illustrated in FIG. 2B. Thus, it is possible to form a first gap region NG1 planar to substrate 2 between opposed-to-gap lower surface 12a and gap-forming upper surface 11a of the first electrode part 3.

In addition to such a configuration as described above, an opposed-to-gap optionally apical surface 12b of second electrode-side gap-forming part 4b may be disposed oppositely to gap-forming side surface 11b of thick-film part 3c of first electrode part 3, as illustrated in FIGS. 1, 2A and 2B. Thus in some embodiments, it is possible to form a second gap region NG2 disposed perpendicularly to substrate 2 (in an y-z plane intersecting at right angles with the plane of substrate 2), the terminal end of second gap region NG2 connecting or overlapping with the first gap region NG1, between opposed-to-gap optionally apical surface 12b and gap-forming side surface 11b of first electrode part 3.

As described herein, a nano-gap NG composed of first gap region NG1 between gap-forming upper surface 11a and opposed-to-gap lower surface 12a and second gap region NG2 between gap-forming side surface 11b and opposed-to-gap optionally apical surface 12b may be formed between first electrode part 3 and second electrode part 4. A nano-gap NG formed between first electrode part 3 and second electrode part 4 may penetrate therethrough toward the y direction intersecting at right angles with the x-z plane. Thus, a nano-gap electrode pair 1 may allow, for example, a solution or the like flowing in the y direction above substrate 2 to pass through a nano-gap NG (first gap region NG1 and second gap region NG2).

Nano-gap NG may be formed such that a width W1 of first gap region NG1 between gap-forming upper surface 11a and opposed-to-gap lower surface 12a and a width W1 of second gap region NG2 between gap-forming side surface 11b and opposed-to-gap optionally apical surface 12b may be almost the same thickness as insulating layer 6. A nano-gap NG may be formed so that width W1 is from about 0.1 nanometers (nm) to 50 nm, 0.5 nm to 30 nm, or 0.5 nm or 10 nm, 0.5 nm to 5 nm, or 0.5 nm to 2 nm, or no greater than 2 nm, 1 nm, 0.9 nm, 0.8 nm, 0.7 nm, 0.6 nm, or 0.5 nm. In some cases, the width of a nanogap can be less than a diameter of a biomolecule or a subunit (e.g., monomer) of the biomolecule.

In some embodiments, a nano-gap electrode pair 1 as described above, may be utilized with a constant voltage applied between first electrode part 3 and second electrode part 4 by, for example, an power supply (not shown) and, under that condition, a solution containing single stranded DNA may be flowed through nano-gap NG between first electrode part 3 and second electrode part 4. The values of currents flowing between first electrode part 3 and second electrode part 4 when single stranded DNA passes through nano-gap NG between first electrode part 3 and second electrode part 4 may be measured with an ammeter (not shown). Thus nano-gap electrode pair 1 may allow a nucleotide sequence of single stranded DNA to be determined from a change in the current values.

In other embodiments utilizing a nano-gap electrode pair 1, a sample may be analyzed at high sensitivity by selecting a nano-gap NG between first electrode part 3 and second electrode part 4 to have a small width W1. In some embodiments a solution containing single stranded DNA may pass through not only first gap region NG1 parallel to substrate 2 but also second gap region NG2 disposed perpendicularly to substrate 2. Thus, a large amount of solution can easily pass through nano-gap NG.

Next, a description will be made of a method for manufacturing a nano-gap electrode pair 1 of FIG. 1. First, a substrate 2 in which, for example, a silicon oxide layer 9 may be formed on a silicon substrate 8 may be prepared. Then, an electrode-forming titanium nitride (TiN) film may be formed on the entire surface or a portion thereof of silicon oxide layer 9 by, for example, a vapor phase deposition method, such as chemical vapor deposition (CVD) or atomic layer deposition (ALD).

Figure 3A:
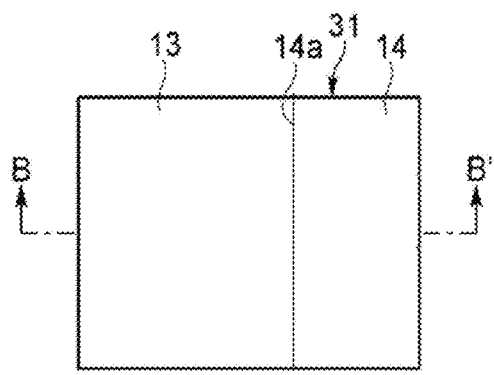
FIGS. 3A-3F are schematic views of a method for manufacturing a nano-gap electrode pair.
Figure 3B:
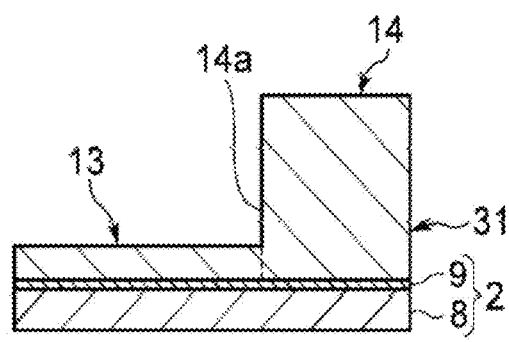

Next, the electrode-forming layer is patterned using a photolithographic technique and, as illustrated in FIG. 3A and FIG. 3B showing lateral cross-section B-B' of FIG. 3A, a predetermined region of a surface of the electrode-forming layer is etched to provide a level difference. Thus, there is formed a first electrode-forming part 31 including a thin-film region 13 thin in film thickness and recessed into an optionally quadrilateral shape, and an optionally quadrilateral thick-film region 14 thicker in film thickness than thin-film region 13 and having a side surface 14a corresponding in height to a difference thickness between thin-film region 13 and thick-film region 14. In a later process, thin-film part 3a of first electrode part 3 and first electrode-side gap-forming part 3b may be formed from thin-film region 13 of first electrode-forming part 31 formed at this time by etching. Likewise, thick-film part 3c of first electrode part 3 can be formed from thick-film region 14 in a later process.

Subsequently, an insulating layer made from, for example, alumina ($Al_2O_3$) may be formed on the entire surface of first electrode-forming part 31 by, for example, a vapor phase deposition method (e.g., CVD). Then, the insulating layer may be patterned using a photolithographic technique and, as illustrated in FIG. 3C and FIG. 3D showing lateral cross-section C-C' of FIG. 3C, a predetermined region of a surface of the insulating layer may be etched, thereby forming an insulating layer 7 on thin-film region 13 of first electrode-forming part 31.

Figure 3C:
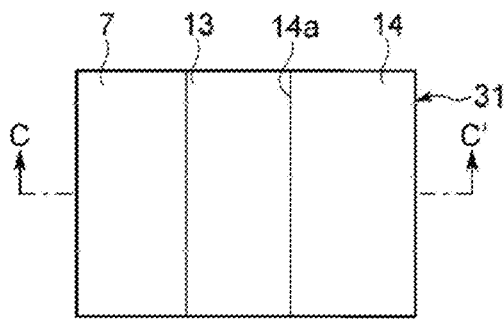
Figure 3D:
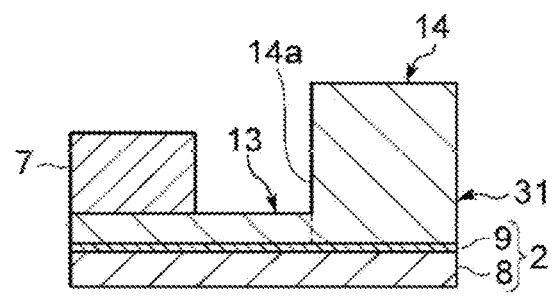
Figure 3E:
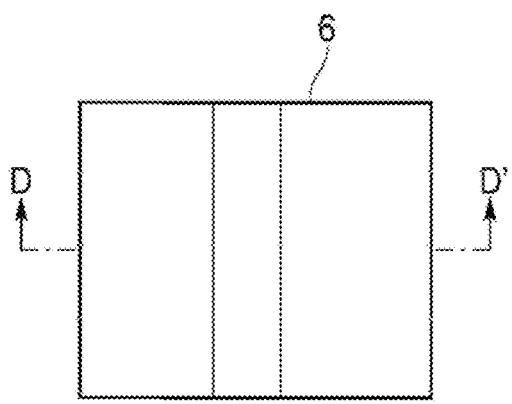
Figure 3F:
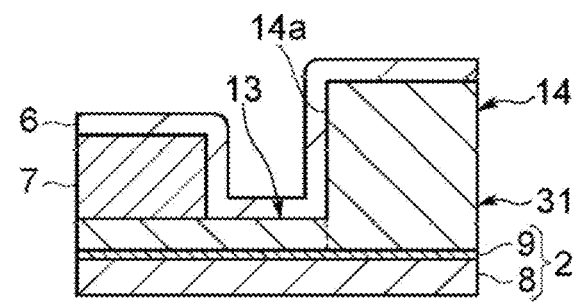

Subsequently, as illustrated in FIG. 3E in which constituent elements corresponding to those of FIG. 3C are denoted by like reference numerals and characters and FIG. 3F showing the lateral cross-section D-D' of FIG. 3E, an insulating layer 6, which may be made, for example, from silicon nitride (SiN), may be formed on the entire surfaces of insulating layer 7 and first electrode-forming part 31 having a level difference between different sections thereof by, for example, a vapor phase deposition method (e.g., CVD). Thus, insulating layer 6 having a level difference almost the same as the level difference formed in first electrode-forming part 31 may be disposed on first electrode-forming part 31. In this case, it is possible to form insulating layer 6 coplanar to substrate 2 on the upper surfaces of thin-film region 13 and thick-film region 14 of first electrode-forming part 31 and extending perpendicularly to substrate 2 on side surface 14a of first electrode-forming part 31. It is also possible to form insulating layer 6 coplanar to substrate 2 on upper surface of insulating layer 7 and extending perpendicularly to substrate 2 on a side surface of insulating layer 7. Insulating layer 6 illustrated by way of example in FIG. 3F may be formed in a conformal manner along first electrode-forming part 31 on which insulating layer 7 is formed, and portions of insulating layer 6 formed on thin-film region 13 and alongside surface 14a, which may have almost the same in film thickness.

Figure 4A:
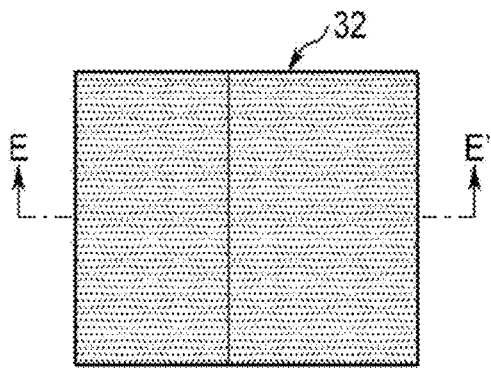
FIGS. 4A-4F are schematic views of a method for manufacturing a nano-gap electrode pair.
Figure 4B:
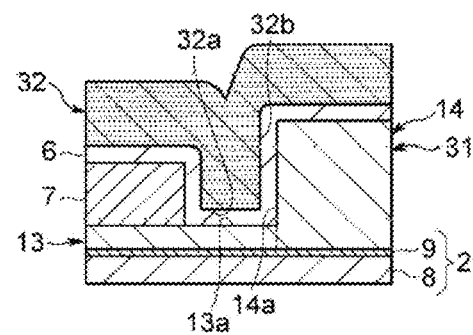

Subsequently, as illustrated in FIG. 4A in which constituent elements corresponding to those of FIG. 3E are denoted by like reference numerals and characters and FIG. 4B showing lateral cross-section E-E' of FIG. 4A, a layer-like second electrode-forming part 32, which may be made from titanium nitride (TiN), may be formed on the entire surface of the insulating layer 6 by, for example, a vapor phase deposition method (e.g., CVD). Consequently, an opposing lower surface 32a opposed to surface 13a of thin-film region 13 of first electrode-forming part 31 and an opposing side surface 32b opposed to side surface 14a of thick-film region 14 of first electrode-forming part 31 can be formed in second electrode-forming part 32.

Figure 4C:
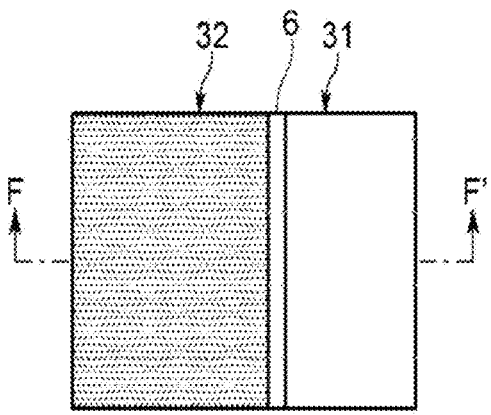
Figure 4D:
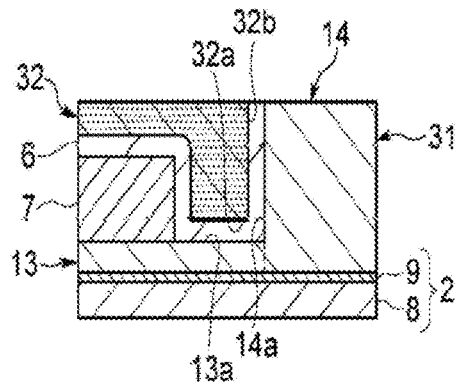

Subsequently, second electrode-forming part 32, insulating layer 6 on thick-film region 14 of first electrode-forming part 31, and thick-film region 14 of first electrode-forming part 31 may be overpolished using, for example, planarization processing, such as chemical mechanical polishing (CMP), and may thereby leave second electrode-forming part 32 in thin-film region 13 of first electrode-forming part 31 and expose a surface of the thick-film region 14 of first electrode-forming part 31, as illustrated in FIG. 4C in which constituent elements corresponding to those of FIG. 4A are denoted by like reference numerals and characters and FIG. 4D showing lateral cross-section F-F' of FIG. 4C. Thus, a surface of the portion of insulating layer 6 extending perpendicularly to substrate 2 may be exposed from between first electrode-forming part 31 and second electrode-forming part 32.

In some embodiments, planarization processing, such as chemical mechanical polishing (CMP), may be performed so as to polish or over polish only second electrode-forming part 32 and insulating layer 6 on thick-film region 14 of first electrode-forming part 31, and in some cases polishing first electrode-forming part 31, exposing the top surface of thick-film region 14 of first electrode-forming part 31, insulating layer 6 and second electrode-forming part 32.

Figure 4E:
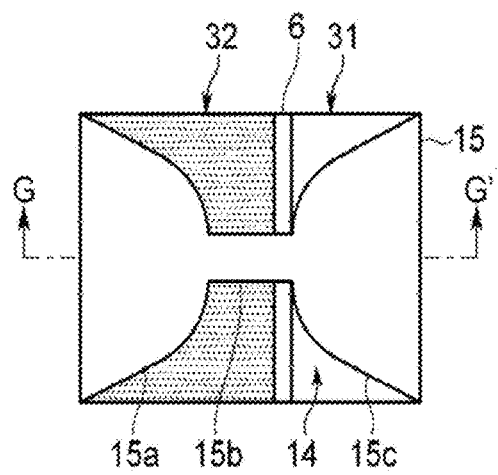
Figure 4F:
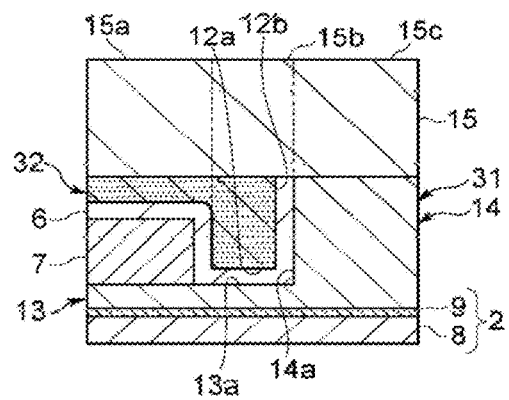

Subsequently, as illustrated in FIG. 4E in which constituent elements corresponding to those of FIG. 4C are denoted by like reference numerals and characters and FIG. 4F showing lateral cross-section G-G' of FIG. 4E, a resist mask 15 patterned using a photolithographic technique may be formed on exposed second electrode-forming part 32, insulating layer 6 and first electrode-forming part 31. Here, resist mask 15 may be formed so that the outer shape thereof conforms to the outer shape of first electrode part 3 illustrated in FIG. 1 which may be subsequently formed.

In some embodiments, resist mask 15 may include a base-forming region 15a formed into a substantially bulbous or tapering shape in conformity with the outer shape of thin-film part 3a of first electrode part 3, a gap-forming region 15b formed into a band shaped shape in conformity with the outer shape of first electrode-side gap-forming part 3b of first electrode part 3, and a base-forming region 15c formed into a substantially bulbous or tapering shape in conformity with the outer shape of thick-film part 3c of the first electrode part 3. Resist mask 15, base-forming region 15a and gap-forming region 15b may be disposed on second electrode-forming part 32, the terminal end of gap-forming region 15b can be disposed on insulating layer 6, and base-forming region 15c can be disposed on thick-film region 14 of first electrode-forming part 31.

Figure 5A:
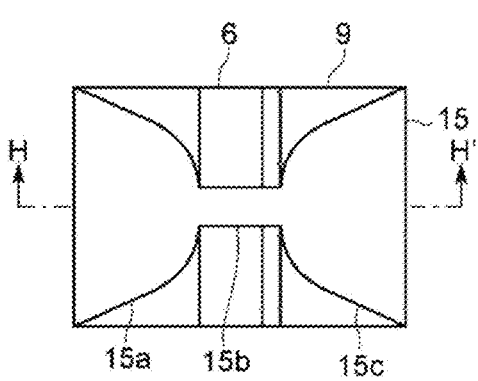
FIGS. 5A-5F are schematic views of a method for manufacturing a nano-gap electrode pair.
Figure 5B:
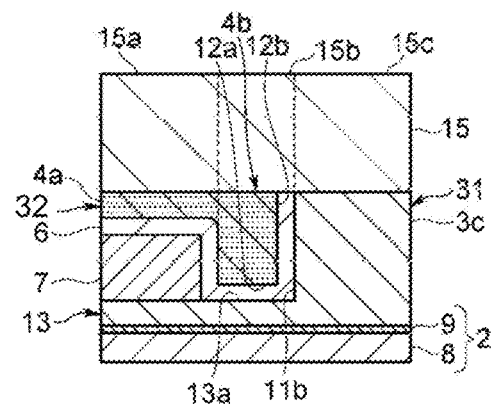

Subsequently, exposed portions of first electrode-forming part 31 and second electrode-forming part 32 not covered by resist mask 15 may be removed by, for example, dry etching. Specifically, as illustrated in FIG. 5A in which constituent elements corresponding to those of FIG. 4E are denoted by like reference numerals and characters and FIG. 5B showing lateral cross-section H-H' of FIG. 5A, second electrode-forming part 32 may be patterned using resist mask 15 to form a second electrode part 4 in a region covered by resist mask 15 and thick-film region 14 of first electrode-forming part 31 may also be patterned using resist mask 15 to form thick-film part 3c in the region covered by resist mask 15.

At this time, base part 4a of second electrode part 4 may be formed as a result of second electrode-forming part 32 being patterned by base-forming region 15a of resist mask 15. Likewise, second electrode-side gap-forming part 4b including opposed-to-gap lower surface 12a and opposed-to-gap optionally apical surface 12b may be formed as a result of second electrode-forming part 32 being patterned by gap-forming region 15b of resist mask 15. In addition, gap-forming side surface 11b opposed to opposed-to-gap optionally apical surface 12b of second electrode part 4 may be formed in thick-film part 3c of first electrode part 3. Silicon oxide layer 9 may be exposed in a region wherein exposed portions of first electrode-forming part 31 not covered by resist mask 15 may be removed. Likewise, insulating layer 6 extending coplanar to substrate 2 and perpendicularly to substrate 2 may be exposed in a region wherein exposed portions of second electrode-forming part 32 not covered by resist mask 15 may be removed. Accordingly, thin-film region 13 of first electrode-forming part 31 covered by insulating layer 6 may not be patterned at this stage.

Figure 5C:
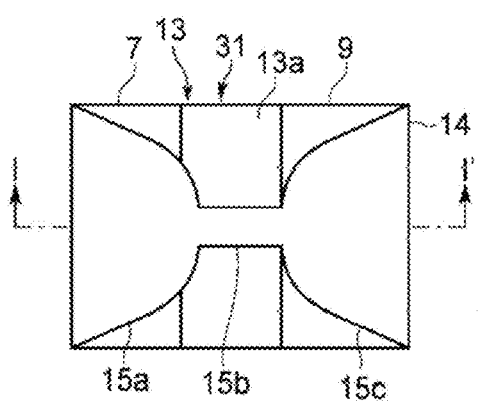
Figure 5D:
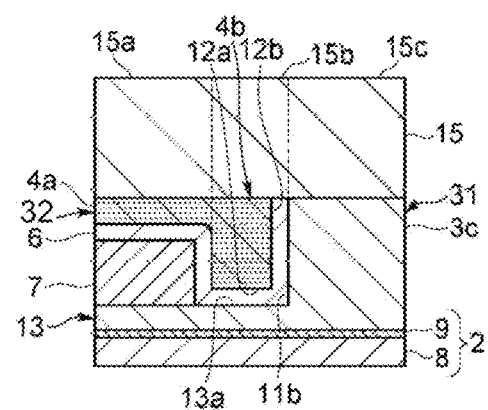

Subsequently, an exposed portion of insulating layer 6 not covered by resist mask 15 may be removed by, for example, dry etching. At this time, dry etching to remove insulating layer 6 may be performed using a gas different from a gas used to remove first electrode-forming part 31 and second electrode-forming part 32 by dry etching. Consequently, as illustrated in FIG. 5C in which constituent elements corresponding to those of FIG. 5A are denoted by like reference numerals and characters and FIG. 5D showing lateral cross-section I-I' of FIG. 5C, insulating layer 7 and thin-film region 13 of first electrode-forming part 31 may be left over and exposed in regions which are not covered by resist mask 15 and from which insulating layer 6 may be removed. In addition, insulating layer 6 may be left over so as to fit the outer shape of second electrode part 4 (base part 4a and second electrode-side gap-forming part 4b) and to stand perpendicularly to substrate 2 between the leading end of second electrode-side gap-forming part 4b and thick-film part 3c of first electrode-forming part 31.

In some embodiments, first electrode-forming part 31 and second electrode-forming part 32 exposed in areas not covered by resist mask 15 may be removed by, for example, dry etching, and then insulating layer 6 may be exposed as a result of removal of second electrode-forming part 32 by another type of etching. In other embodiments, first electrode-forming part 31, second electrode-forming part 32 and insulating layer 6 may be removed in succession by the same type of etching.

In some cases, if an insulating layer 6 having a thin film thickness of, for example, 2 nm is formed, a portion of insulating layer 6 formed underneath second electrode-forming part 32 may be removed at the same time that first electrode-forming part 31 and second electrode-forming part 32 are removed. In this case, surfaces of thin-film region 13 of first electrode-forming part 31 and insulating layer 7 exposed as result of insulating layer 6 being removed may also be etched, and therefore, level differences may be formed in first electrode-forming part 31 and insulating layer 7.

Thereafter, an exposed portion of insulating layer 7 not covered with resist mask may be removed by an anisotropic removal process, for example, dry etching. At this time, dry etching for removing an exposed portion of insulating layer 7 may be performed using a gas different from a gas used to remove first electrode-forming part 31 and second electrode-forming part 32 by dry etching and a gas used to remove insulating layer 6 by dry etching. Consequently, thin-film region 13 of first electrode-forming part 31 may be left over and exposed in a region from where insulating layer 7 is removed.

Figure 5E:
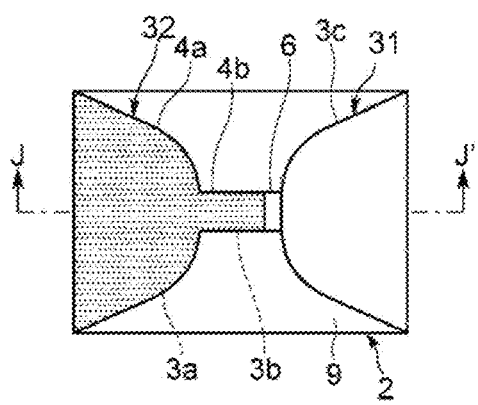
Figure 5F:
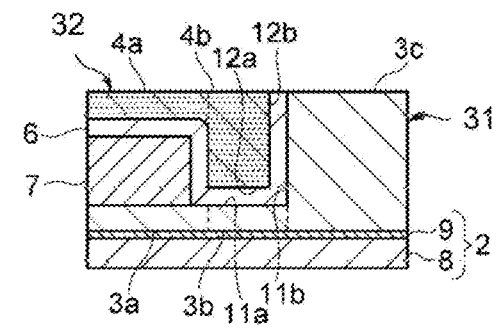

Subsequently, the exposed portion of first electrode-forming part 31 not covered by resist mask 15 may be removed by an anisotropic removal process, for example, dry etching to pattern first electrode-forming part 31, thereby forming first electrode part 3. Thereafter, resist mask 15 may be removed by plasma ashing, or by the use of a liquid resist stripper to expose first electrode part 3 and second electrode part 4 covered by resist mask 15, as illustrated in FIG. 5E in which constituent elements corresponding to those of FIG. 5C are denoted by like reference numerals and characters and FIG. 5F showing lateral cross-section J-J' of FIG. 5E.

Consequently, first electrode part 3 including thin-film part 3a, first electrode-side gap-forming part 3b which may have a thin film thickness, and thick-film part 3c which may have a thick film thickness may be formed on substrate 2. In addition, base part 4a of second electrode part 4 may be disposed above thin-film part 3a of first electrode part 3 as a result of being disposed on insulating layers 7 and 6. Yet additionally, second electrode-side gap-forming part 4b of second electrode part 4 may be disposed above first electrode-side gap-forming part 3b as a result of being disposed on insulating layer 6. First electrode part 3 may be formed such that surfaces of thick-film part 3c and second electrode part 4 may be flush with each other, and thick-film part 3c may be disposed oppositely to second electrode-side gap-forming part 4b so as to align therewith on opposing sides of insulating layer 6 wherein exposed surfaces thereof may be coplanar to substrate 2. That is, second electrode-side gap-forming part 4b may be disposed such that opposed-to-gap lower surface 12a is disposed oppositely to gap-forming upper surface 11a of first electrode-side gap-forming part 3b on opposite sides of insulating layer 6, and opposed-to-gap optionally apical surface 12b may be disposed oppositely to gap-forming side surface 11b of thick-film part 3c on opposite sides of insulating layer 6.

Subsequently, portions of insulating layer 6 between gap-forming upper surface 11a and opposed-to-gap lower surface 12a and between gap-forming side surface 11b and opposed-to-gap optionally apical surface 12b may be removed by, for example, a time controlled wet etching. Consequently, as illustrated in FIG. 1, FIG. 2A and FIG. 2B, first gap region NG1 coplanar to substrate 2 may be formed between gap-forming upper surface 11a and opposed-to-gap lower surface 12a. In addition, a second gap region NG2, extending perpendicularly to substrate 2, the lower terminal end of second gap region NG2 being connected or overlapping with first gap region NG1, may be formed between gap-forming side surface 11b and opposed-to-gap optionally apical surface 12b. In this way, it is possible to manufacture nano-gap electrode pair 1 including nano-gap NG comprising of first gap region NG1 and second gap region NG2.

A nano-gap electrode pair 1 manufactured by a manufacturing method as described herein, a film thickness of insulating layer 6 formed between first electrode part 3 and second electrode part 4 may serve to form width W1 of nano-gap NG formed between first electrode part 3 and second electrode part 4. Accordingly, a nano-gap NG having a desired width may be easily manufactured simply by adjusting a film thickness of insulating layer 6 in the course of manufacture. In addition, since insulating layer 6 can be formed to have an extremely thin film thickness, it is possible to also proportionally decrease width W1 of nano-gap NG to be formed between first electrode part 3 and second electrode part 4.

In some cases, a portion of insulating layer 6 located between thin-film part 3a of first electrode part 3 and base part 4a of second electrode part 4 may also come into contact with a chemical solution used for wet etching at the time of removing a portion of insulating layer 6 located between first electrode-side gap-forming part 3b of first electrode part 3 and second electrode-side gap-forming part 4b of second electrode part 4. In such a case, the outer circumferential surface of insulating layer 6 under base part 4a may be etched. As a result, insulating layer 6 may be formed with a slightly smaller outer periphery than thin-film part 3a and base part 4a. In addition, due to the greater width a portion of insulating layer 6 formed between a side surface of insulating layer 7 and second electrode-side gap-forming part 4b of second electrode part 4 may be less likely to come into contact with a chemical solution used for a time limited wet etching and may, therefore, remain without being etched away.

In some embodiments, —a gap electrode 1 may comprise a, first electrode part 3 including first electrode-side gap-forming part 3b which may have a thin film thickness may be disposed between thin-film part 3a and thick-film part 3c on substrate 2, and second electrode part 4 may be disposed above thin-film part 3a and may be disposed on insulating layers 7 and 6. In some embodiments, nano-gap electrode pair 1 may comprise a second electrode-side gap-forming part 4b formed as a part of second electrode part 4 which may be disposed oppositely to first electrode-side gap-forming part 3b of first electrode part 3, and first gap region NG1 coplanar to substrate 2 may be formed between first electrode-side gap-forming part 3b and second electrode-side gap-forming part 4b. In some embodiments a nano-gap electrode pair 1 may comprise a leading end of second electrode-side gap-forming part 4b of second electrode part 4 which may be disposed oppositely to thick-film part 3c of first electrode part 3, and second gap region NG2 extending perpendicularly to the substrate 2, the terminal end of second gap region NG2 which may connect or overlap with first gap region NG1, may be formed between second electrode-side gap-forming part 4b and thick-film part 3c.

Consequently, utilizing a nano-gap electrode pair 1, a sample may be analyzed with high sensitivity by forming a nano-gap NG between first electrode part 3 and second electrode part 4 so as to have a small width W1. In addition, a solution containing single stranded DNA may be allowed to pass through not only first gap region NG1 parallel to substrate 2 but also second gap region NG2 disposed perpendicularly to substrate 2 wherein nano-gap NG between first electrode part 3 and second electrode part 4 may be selected so as to have a small width W1. Thus, a larger amount of solution may easily pass through nano-gap NG.

In some embodiments, a first electrode-forming part 31 with a multiple levels and an insulating layer 7 may be initially formed on a substrate 2. Then, an insulating layer 6 coplanar to substrate 2 and perpendicular thereto may be formed on portions of first electrode-forming part 31 and insulating layer 7. Subsequently, a second electrode-forming part 32 may be formed on insulating layer 6, then an upper surface of first electrode-forming part 31, a surface of a portion of the insulating layer 6 extending perpendicularly to substrate 2, and a surface of the second electrode-forming part 32 may be exposed by for example, a CMP process, to pattern second electrode-forming part 32, insulating layer 6, insulating layer 7, and first electrode-forming part 31 using resist mask 15.

Subsequently, it is possible to form a first electrode part 3 and a second electrode part 4 having predetermined shapes. In addition, an insulating layer 6 coplanar to substrate 2 and perpendicular thereto may be formed between first electrode part 3 and second electrode part 4. Finally, a portion of insulating layer 6 between first electrode part 3 and second electrode part 4 may be removed to form a nano-gap NG composed of a first gap region NG1 coplanar to substrate 2 and a second gap region NG2 extending perpendicularly to substrate 2, the terminal end of second gap region NG2 connecting or overlapping with first gap region NG1, between first electrode part 3 and second electrode part 4.

In this way, it is possible to manufacture a nano-gap electrode pair 1 wherein a solution can pass through not only first gap region NG1 but also second gap region NG2, even if a width W1 of nano-gap NG between first electrode part 3 and second electrode part 4 is made to be substantially small, and therefore, a solution containing single stranded DNA which may be measured using the nano-gap NG may all the more easily pass through nano-gap NG, than if nano-gap NG had a single nano-gap region.

In some embodiments utilizing a manufacturing method, it is possible to easily adjust a width W1 of nano-gap NG between first electrode part 3 and second electrode part 4 simply by adjusting film thickness of insulating layer 6. In addition, since insulating layer 6 may be formed to have an extremely thin film thickness using this manufacturing method, it is possible to easily and routinely form a nano-gap NG (which may comprise first gap region NG1 and second gap region NG2) having an extremely small width W1 corresponding to a film thickness of insulating layer 6.

Figure 6:
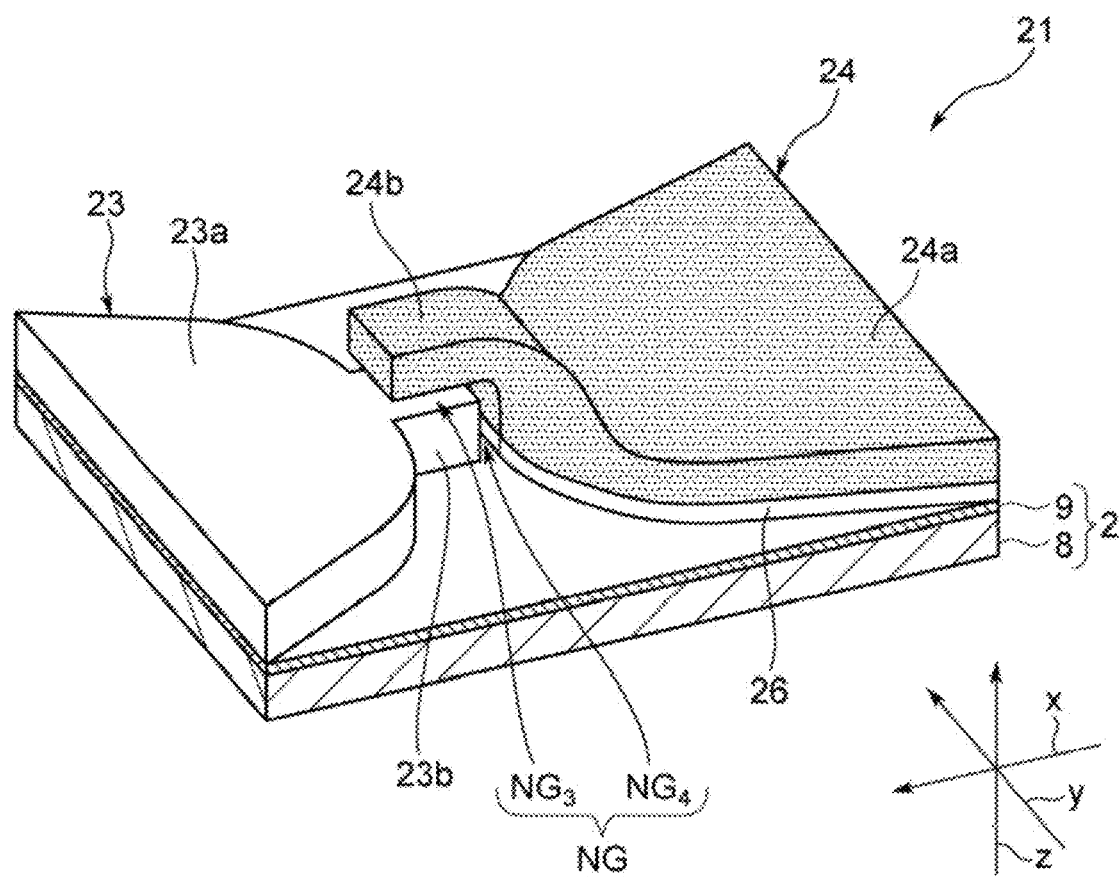
FIG. 6 is a schematic view illustrating the overall configuration of a nano-gap electrode pair.

In FIG. 6 in which constituent elements corresponding to those of FIG. 1 are denoted by like reference numerals and characters, reference numeral 21 denotes a nano-gap electrode pair which differs from the nano-gap electrode pair of FIG. 1 in that the lateral cross-sectional shape of a nano-gap NG is formed into a substantially inverted-L shape. In some embodiments a nano-gap NG may be comprised of a first gap region NG3 extending in two directions; disposed coplanar to substrate 2 and a second gap region NG4 disposed perpendicularly to substrate 2, the terminal end of second gap region NG4 overlapping with first gap region NG3, may be formed between a first electrode part 23 and a second electrode part 24.

In some embodiments, first electrode part 23 may be disposed on silicon oxide layer 9 which may be a part of substrate 2, second electrode part 24, forming a pair with first electrode part 23, may be disposed above silicon oxide layer 9 on conductive layer 26 which may serve as a gap-forming layer, and a second electrode-side gap-forming part 24b of second electrode part 24 may be disposed above a band shaped first electrode-side gap-forming part 23b of first electrode part 23 on substrate 2, so as to overlap first electrode-side gap-forming part 23b. Accordingly, a hollow nano-gap NG, the width of which may be nanoscale (no greater than, for example, 1000 nm) may be formed between first electrode-side gap-forming part 23b and second electrode-side gap-forming part 24b.

Figure 7A:
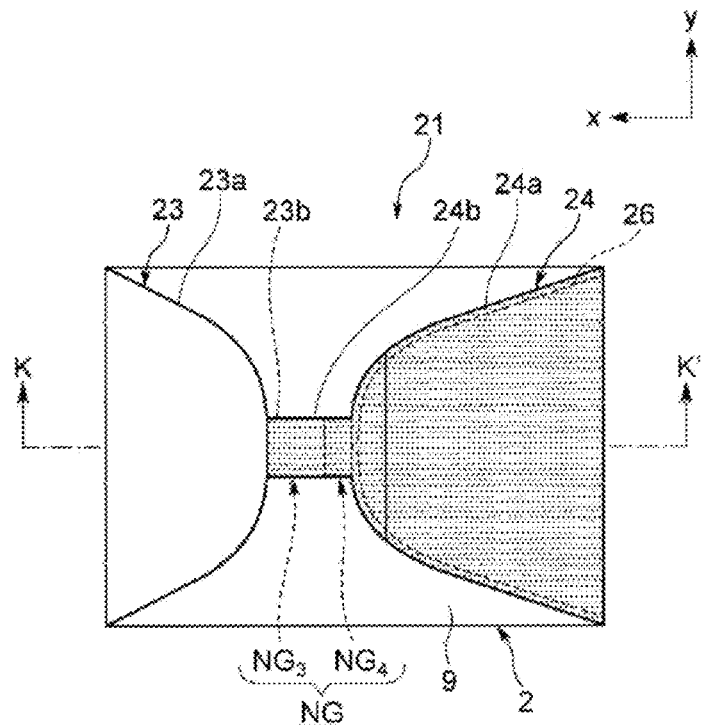
FIG. 7A is a top view illustrating the upper-surface configuration of a nano-gap electrode pair of FIG. 6.
Figure 7B:
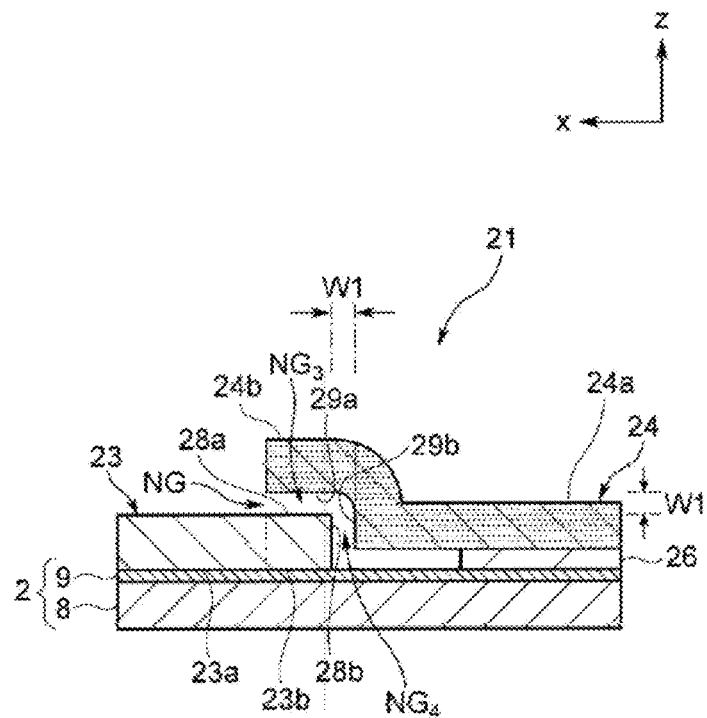
FIG. 7B is a cross-sectional side view illustrating a lateral cross-sectional configuration of a nano-gap electrode pair of FIG. 6.

In some embodiments, first electrode part 23 may be formed from a metal material, such as titanium nitride (TiN), and may include a base part 23a formed into a predetermined shape, and a first electrode-side gap-forming part 23b, one side of which may be formed integrally with base part 23a. Base part 23a of first electrode part 23 illustrated in FIG. 6 may have a configuration in which the outer shape of base part 23a may be formed into a substantially bulbous or tapered shape as illustrated in FIG. 7A which shows a top view of the device of FIG. 6, wherein one end of band shaped first electrode-side gap-forming part 23b may be formed integrally with the central leading end of base part 23a. As illustrated in FIG. 7B which shows lateral cross-section K-K' of FIG. 7A, first electrode-side gap-forming part 23b may include a planar gap-forming upper surface 28a coplanar to substrate 2, and a planar gap-forming optionally apical surface 28b extending perpendicularly to substrate 2 from the terminal end of gap-forming upper surface 28a. Gap-forming upper surface 28a and gap-forming optionally apical surface 28b may be disposed oppositely to second electrode part 24 with nano-gap NG interposed therebetween.

Second electrode part 24 may be formed from a metal material, such as titanium nitride (TiN), and may include a base part 24a disposed above substrate 2 on conductive layer 26, and second electrode-side gap-forming part 24b may be formed integrally with base part 24a and which may be formed so as to overlap first electrode-side gap-forming part 23b of first electrode part 23 with nano-gap NG interposed therebetween. In some embodiments, conductive layer 26 may be formed from an electroconductive material, such as titanium (Ti), which may be etched using different etching conditions from those etching conditions used to etch silicon oxide layer 9.

In some embodiments, conductive layer 26 has an outer shape which may be almost the same as the outer shape of base part 24a of second electrode part 24, as shown by a dotted line in FIG. 7A. However, the outer circumferential surface of the conductive layer 26 may be etched by wet etching performed at the time of nano-gap formation in the course of manufacture (described later), and therefore, conductive layer 26 may be formed to be slightly smaller in outer shape than base part 24a.

In some embodiments, the outer shape of base part 24a of second electrode part 24, illustrated by way of example in FIGS. 6 and 7A, may be formed into a substantially bulbous or tapered shape symmetrical to the outer shape of base part 23a of first electrode part 23, and the root of band shaped second electrode-side gap-forming part 24b may be formed integrally with the central leading end of base part 24a. In addition, as illustrated in FIG. 7B, second electrode-side gap-forming part 24b may be disposed so as to conform in outer periphery to first electrode-side gap-forming part 23b, and may be disposed oppositely to first electrode-side gap-forming part 23b with nano-gap NG interposed therebetween.

In some embodiments, second electrode-side gap-forming part 24b may comprise an opposed-to-gap lower surface 29a which may be disposed oppositely to gap-forming upper surface 28a of first electrode-side gap-forming part 23b, and first gap region NG3 may be formed between this opposed-to-gap lower surface 29a and gap-forming upper surface 28a coplanar to substrate 2. In addition, second electrode part 24 may include an opposed-to-gap side surface 29b extending from opposed-to-gap lower surface 29a toward substrate 2 as a part of base part 24a. Thus, it is possible to dispose opposed-to-gap side surface 29b oppositely to gap-forming optionally apical surface 28b of first electrode-side gap-forming part 23b, and form second gap region NG4 disposed perpendicularly to substrate 2, the terminal end of second gap region NG4 connecting or overlapping with the first gap region NG3, between opposed-to-gap side surface 29b and gap-forming optionally apical surface 28b.

As described herein, nano-gap electrode pair 21 may be configured so that nano-gap NG may comprise first gap region NG3 located between gap-forming upper surface 28a and opposed-to-gap lower surface 29a and second gap region NG4 located between gap-forming optionally apical surface 28b and opposed-to-gap side surface 29b may be formed between first electrode part 23 and second electrode part 24. Nano-gap NG formed between first electrode part 23 and second electrode part 24 may penetrate therethrough toward the y direction intersecting at right angles with the x-z plane. Thus, nano-gap electrode pair 21 may allow a solution or the like flowing in the y direction on substrate 2 to pass through nano-gap NG (which may comprise first gap region NG3 and second gap region NG4).

In some embodiments, a side surface of conductive layer 26 and gap-forming optionally apical surface 28b of first electrode-side gap-forming part 23b may be disposed oppositely to each other, and a nano-gap may be formed in a region between opposed-to-gap side surface 29b and gap-forming optionally apical surface 28b. Conductive layer 26 having electrical conductivity may function as an electrode, and therefore, conductive layer 26 may also function as a nano-gap electrode pair.

In some embodiments, width W1 of first gap region NG3 between gap-forming upper surface 28a and opposed-to-gap lower surface 29a and width W1 of second gap region NG4 between gap-forming optionally apical surface 28b and opposed-to-gap side surface 29b may have almost the same dimensions as the film thickness of conductive layer 26, as illustrated in FIG. 7B. Thus, gap regions may be formed to a width W1 that is from about 0.1 nanometers (nm) to 50 nm, 0.5 nm to 30 nm, or 0.5 nm or 10 nm, 0.5 nm to 5 nm, or 0.5 nm to 2 nm, or no greater than 5 nm, 4 nm, 3 nm, 2 nm, 1 nm, 0.9 nm, 0.8 nm, 0.7 nm, 0.6 nm, or 0.5 nm. In some cases, the width of a nanogap can be less than a diameter of a biomolecule or a subunit (e.g., monomer) of the biomolecule.

In some embodiments, with respect to the nano-gap electrode pair 21, a voltage, which may be a constant voltage, may be applied between first electrode part 23 and second electrode part 24 by, for example, a power supply (not shown) and, under that condition, a solution containing single or double stranded DNA may be guided by a guiding member (not shown) such as electrophoretic or pressure system, so as to be able to flow the single or double stranded DNA through nano-gap NG between first electrode part 23 and second electrode part 24. Values of currents flowing between first electrode part 23 and second electrode part 24 when single stranded DNA carried by the flow of the solution, or electrophoretic induced motion pass through nano-gap NG between first electrode part 23 and second electrode part 24 may be measured with an ammeter. Thus, nano-gap electrode pair 21 allows the nucleotide sequence of single stranded, or double stranded DNA to be determined from changes in current values.

In some embodiments nano-gap electrode pair 21 may be utilized to analyze a sample with high sensitivity by selecting or forming nano-gap NG width between first electrode part 23 and second electrode part 24 to be a small width W1. A solution containing single stranded or double stranded DNA is allowed to pass through not only first gap region NG3 coplanar to substrate 2 but also second gap region NG4 disposed perpendicularly to substrate 2. Thus, larger amounts of solution may pass through the nano-gap NG.

Figure 8A:
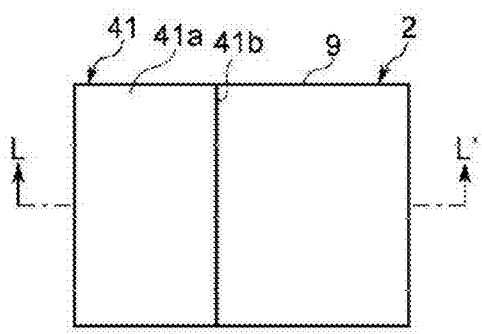
FIGS. 8A-8F are schematic views of a method for manufacturing the nano-gap electrode pair of FIG. 6.
Figure 8B:
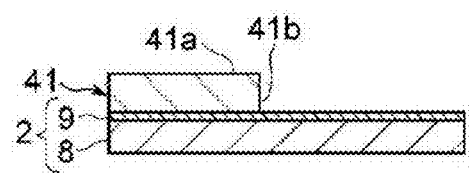

In some embodiments as shown in top view FIG. 8A illustrating nano-gap electrode pair 21, and in FIG. 8B showing cross-section L-L' of FIG. 8A. First, as illustrated in FIGS. 8A and 8B, a substrate 2 comprising, for example, a silicon oxide layer 9 which may be formed on silicon substrate 8 may be prepared, and then a first electrode-forming part 41 made from, for example, titanium nitride (TiN) and patterned into, for example, a quadrilateral shape using a photolithographic technique may be formed on silicon oxide layer 9. In some embodiments, a side surface 41b having a height corresponding to a film thickness of first electrode-forming part 41 may be formed by an edge surface of first electrode-forming part 41 between upper surface 41a and substrate 2 as a part of patterned first electrode-forming part 41. First electrode-forming part 41 formed in this way may be patterned in a later process into base part 23a and first electrode-side gap-forming part 23b of first electrode part 23.

Figure 8C:
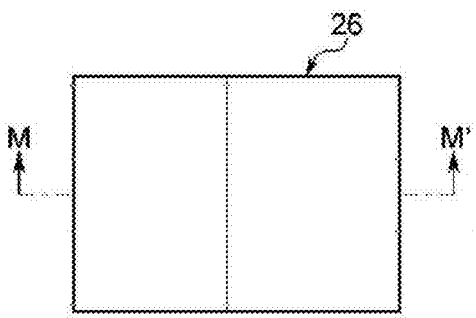
Figure 8D:
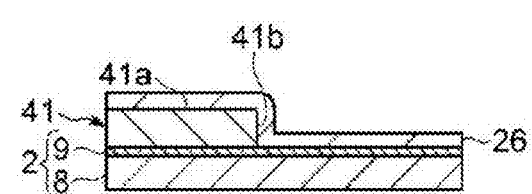

Subsequently, as illustrated in FIG. 8C in which constituent elements corresponding to those of FIG. 8A are denoted by like reference numerals and characters and FIG. 8D shows lateral cross-section M-M' of FIG. 8C, conductive layer 26, which may be made from titanium (Ti), may be formed on first electrode-forming part 41 including on side surface 41b and on substrate 2 by, for example, a vapor phase deposition method (e.g., CVD). Consequently, a level difference almost the same as a level difference formed by an edge of first electrode-forming part 41 between substrate 2 and side surface 41b of first electrode-forming part 41, may be formed by a surface of conductive layer 26.

In some embodiments, conductive layer 26 may be formed on upper surface 41a of first electrode-forming part 41 and on substrate 2 coplanar to substrate 2. In addition, a portion of conductive layer 26 extending perpendicularly to substrate 2 may be formed on side surface 41b of first electrode-forming part 41. Conductive layer 26 illustrated by way of example in FIG. 8D may be formed in a conformal manner along first electrode-forming part 41 and substrate 2, and portions of conductive layer 26 formed on upper surface 41a of first electrode-forming part 41 and alongside surface 41b may have almost the same film thickness.

Figure 8E:
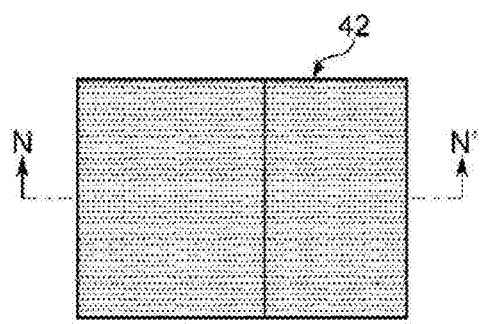
Figure 8F:
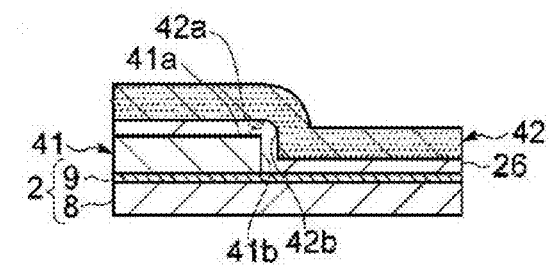

Subsequently, as illustrated in FIG. 8E in which constituent elements corresponding to those of FIG. 8C are denoted by like reference numerals and characters and FIG. 8F showing lateral cross-section N-N' of FIG. 8C, a layer-like second electrode-forming part 42 made from titanium nitride (TiN) may be formed on the entire surface of the conductive layer 26 or a portion thereof by, for example, a vapor phase deposition method (e.g., CVD). Here, a level difference almost the same as a level difference formed in conductive layer 26 may be formed in second electrode-forming part 42. Consequently, an opposing lower surface 42a opposed to upper surface 41a of first electrode-forming part 41 through the conductive layer 26 and an opposing side surface 42b opposed to the side surface 41b of the first electrode-forming part 41 through the conductive layer 26 are formed in the bottom face of the second electrode-forming part 42.

Figure 9A:
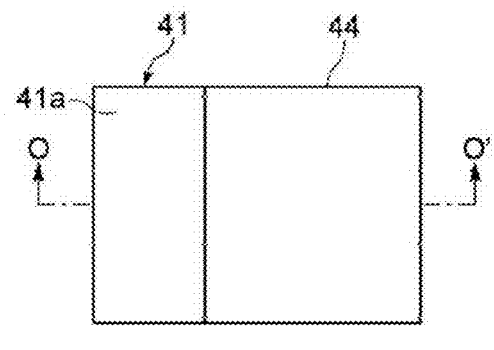
FIGS. 9A-9F are schematic views of a method for manufacturing the nano-gap electrode pair of FIG. 6.
Figure 9B:
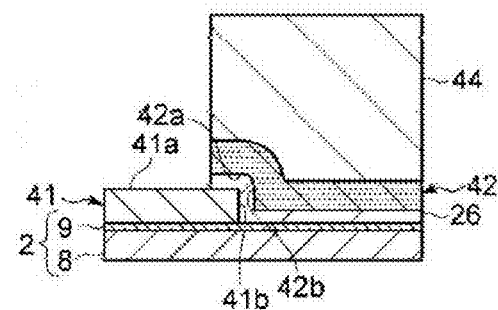

Subsequently, as illustrated in FIG. 9A in which constituent elements corresponding to those of FIG. 8E are denoted by like reference numerals and characters and FIG. 9B showing lateral cross-section O-O' of FIG. 9A, second electrode-forming part 42 and conductive layer 26 may be patterned with a resist mask 44 patterned using a photolithographic technique to overlap conductive layer 26 and second electrode-forming part 42 over at least a part of upper surface 41a of first electrode-forming part 41 and over a region of substrate 2 wherein first electrode-forming part 41 may not be formed.

In some embodiments, a portion of second electrode-forming part 42 exposed in an area not covered by resist mask 44 may be removed by an anisotropic etching process, for example, dry etching. A portion of conductive layer 26 thus exposed may also be removed in succession by the same dry etching. Another type of dry etching may be applied to second electrode-forming part 42 and conductive layer 26 utilizing different conditions. If conductive layer 26 has a thin film thickness of, for example, 2 nm, a surface of first electrode-forming part 41 formed underneath conductive layer 26 may also be etched when second electrode-forming part 42 and conductive layer 26 are removed. In this case, a level difference may be formed in the upper surface 41a of the first electrode-forming part 41.

Thereafter, the resist mask 44 is removed by plasma ashing, or by the use of a liquid resist stripper to expose second electrode-forming part 42 covered by resist mask 44. Subsequently, as illustrated in FIG. 9C in which constituent elements corresponding to those of FIG. 9A are denoted by like reference numerals and characters and FIG. 9D showing lateral cross-section P-P' of FIG. 9C, a region upon which conductive layer 26 and second electrode-forming part 42 are formed and a region wherein upper surface 41a may be exposed may be formed on at least a part of upper surface 41a of first electrode-forming part 41.

Figure 9C:
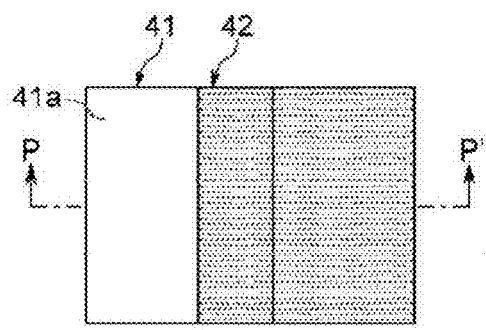
Figure 9D:
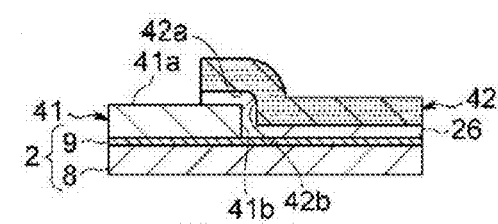
Figure 9E:
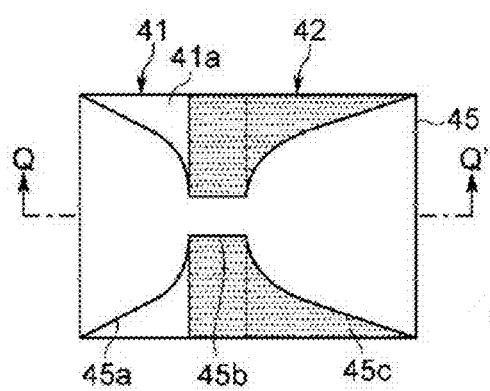
Figure 9F:
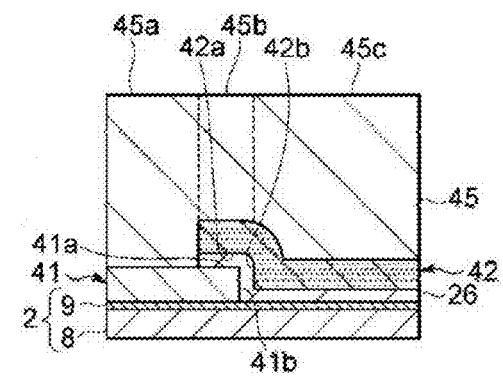

Subsequently, as illustrated in FIG. 9E in which constituent elements corresponding to those of FIG. 9C are denoted by like reference numerals and characters and FIG. 9F showing lateral cross-section Q-Q' of FIG. 9E, a new resist mask 45 which may be patterned using a photolithographic technique may be disposed over an area covering a portion of exposed first electrode-forming part 41 and second electrode-forming part 42. Resist mask 45 may be formed into a shape which is a combination of the outer shapes of first electrode part 23 and second electrode part 24 illustrated in FIG. 6 which will be formed subsequently.

In some embodiments, resist mask 45 may include a base-forming region 45a formed into a substantially bulbous or tapered shape in conformity with outer shape of base part 23a of first electrode part 23, a gap-forming region 45b formed into a band shaped shape in conformity with the outer shapes of first electrode-side gap-forming part 23b and second electrode-side gap-forming part 24b, and a base-forming region 45c formed into a substantially bulbous or tapered shape in conformity with the outer shape of base part 24a of second electrode part 24. Base-forming region 45a of the resist mask 45 may be disposed on upper surface 41a of first electrode-forming part 41 where second electrode-forming part 42 may not be present, and base-forming region 45c and gap-forming region 45b of resist mask 45 may be disposed on second electrode-forming part 42.

Figure 10A:
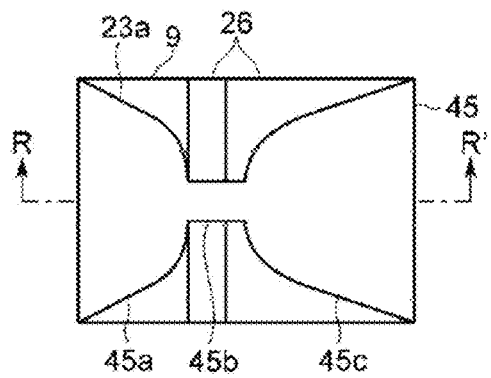
FIGS. 10A-10F are schematic views of a method for manufacturing a nano-gap electrode pair of FIG. 6.
Figure 10B:
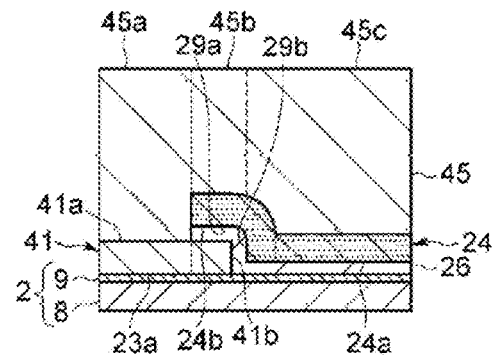

Subsequently, exposed portions of first electrode-forming part 41 and second electrode-forming part 42 not covered with resist mask 45 may be removed by, for example, dry etching. Thus, base part 23a may be formed from first electrode-forming part 41, and second electrode part 24 comprising base part 24a and second electrode-side gap-forming part 24b may be formed from second electrode-forming part 42, as illustrated in FIG. 10A in which constituent elements corresponding to those of FIG. 9E are denoted by like reference numerals and characters and FIG. 10B showing lateral cross-section R-R' of FIG. 10A.

In some embodiments, base part 24a of second electrode part 24 may be formed as a result of second electrode-forming part 42 being patterned by base-forming region 45c of resist mask 45. Likewise, second electrode-side gap-forming part 24b including opposed-to-gap lower surface 29a and opposed-to-gap side surface 29b may be formed as a result of second electrode-forming part 42 being patterned by gap-forming region 45b of resist mask 45. Silicon oxide layer 9 may be exposed in a region wherein an exposed portion of first electrode-forming part 41 not covered with resist mask 45 may have been removed. Likewise, conductive layer 26 may be exposed in a region from wherein exposed portion of second electrode-forming part 42 not covered with resist mask 45 may have been removed.

Figure 10C:
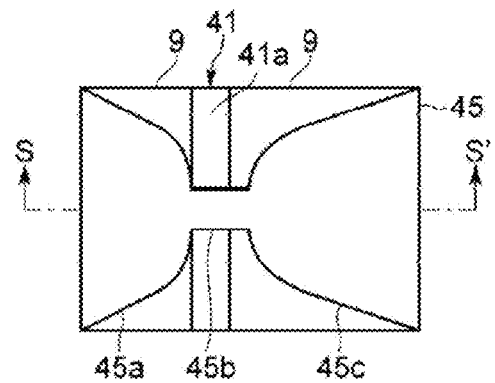
Figure 10D:
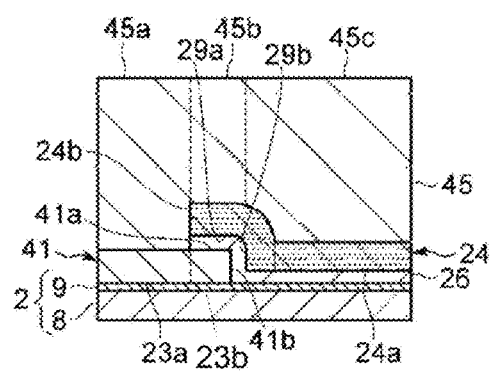

Subsequently, portions of exposed conductive layer 26 not covered by resist mask 45 may be removed by an anisotropic etching process, for example, dry etching. Dry etching utilized for removing conductive layer 26 may be performed using a gas different than a gas used to remove first electrode-forming part 41 and second electrode-forming part 42 used for dry etching. Subsequently, as illustrated in FIG. 10C in which constituent elements corresponding to those of FIG. 10A are denoted by like reference numerals and characters and FIG. 10D showing lateral cross-section S-S' of FIG. 10C, silicon oxide layer 9 may be exposed in a region from where conductive layer 26 on the substrate 2 may have been removed. First electrode-forming part 41 remaining may later form first electrode-side gap-forming part 23b which may be exposed in a region from where conductive layer 26 may be removed.

Figure 10E:
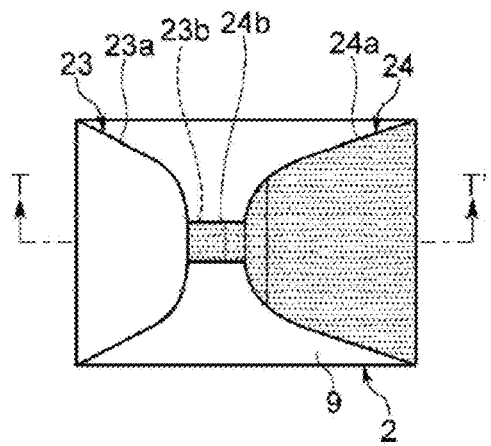
Figure 10F:
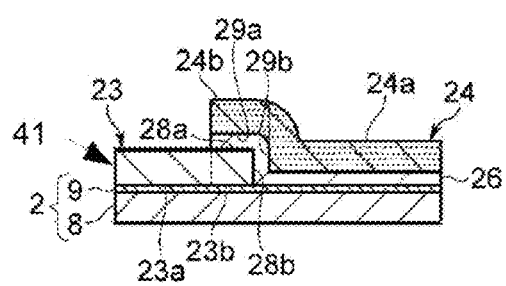

Subsequently, an exposed portion of first electrode-forming part 41 not covered with resist mask 45 may be removed by, for example, dry etching, and then resist mask 45 may be removed by plasma ashing, or by the use of a liquid resist stripper. Consequently, as illustrated in FIG. 10E in which constituent elements corresponding to those of FIG. 10C are denoted by like reference numerals and characters and FIG. 10F showing lateral cross-section T-T' of FIG. 10E, first electrode-forming part 41 may remain in a region wherein gap-forming region 45b of resist mask 45 may have been located, thereby forming first electrode-side gap-forming part 23b including gap-forming upper surface 28a and gap-forming optionally apical surface 28b, and first electrode part 23 provided with first electrode-side gap-forming part 23b.

Gap-forming upper surface 28a of first electrode-side gap-forming part 23b formed as described above may be disposed oppositely to opposed-to-gap lower surface 29a of second electrode-side gap-forming part 24b on opposing sides of conductive layer 26. Likewise, gap-forming optionally apical surface 28b may be disposed oppositely to opposed-to-gap side surface 29b of second electrode-side gap-forming part 24b on opposing sides of conductive layer 26.

Subsequently, portions of conductive layer 26 between gap-forming upper surface 28a and opposed-to-gap lower surface 29a and between gap-forming optionally apical surface 28b and opposed-to-gap side surface 29b may be removed by, for example, wet etching. Consequently, as illustrated in FIGS. 6, 7A and 7B, a first gap region NG3 coplanar to substrate 2 may be formed between gap-forming upper surface 28a and opposed-to-gap lower surface 29a. In addition, a second gap region NG4 extending perpendicularly to substrate 2, the upper terminal end of second gap region NG4 connecting or overlapping with first gap region NG3 may be formed between gap-forming optionally apical surface 28b and opposed-to-gap side surface 29b. In this way, it is possible to manufacture a nano-gap electrode pair 21 including a nano-gap NG comprising of first gap region NG3 and second gap region NG4 and having an inverted L shaped lateral cross-section between first electrode part 23 and second electrode part 24.

In some embodiments, nano-gap electrode pair 21 manufactured according to methods provided herein may utilize a film thickness of conductive layer 26 formed between first electrode part 23 and second electrode part 24 which may serve for form width W1 of nano-gap NG formed between first electrode part 23 and second electrode part 24. Accordingly, a nano-gap NG having a desired width may be easily manufactured simply by adjusting a film thickness of conductive layer 26 in the course of manufacture. In addition, since conductive layer 26 may be formed to have an extremely thin film thickness, it is possible to proportionally decrease a width W1 of nano-gap NG to be formed between first electrode part 23 and second electrode part 24.

In some embodiments, a portion of conductive layer 26 located between the base part 24a of second electrode part 24 and silicon oxide layer 9 may come into contact with a chemical solution used for wet etching at the time of removing a portion of conductive layer 26 located between first electrode-side gap-forming part 23b and second electrode-side gap-forming part 24b, the outer circumferential surface of the conductive layer 26 may be etched. As a result, conductive layer 26 may be formed so as to be slightly smaller in outer periphery than base part 24a.

In some embodiments wherein nano-gap electrode pair 21 may comprise a, first electrode part 23 wherein first electrode-side gap-forming part 23b may be disposed on substrate 2, and second electrode part 24 may be disposed above substrate 2 on conductive layer 26. In further embodiments, a nano-gap electrode pair 21 may comprise a second electrode-side gap-forming part 24b which may be formed in second electrode part 24, and may be disposed oppositely and above to first electrode-side gap-forming part 23b of first electrode part 23, and first gap region NG3 coplanar to substrate 2 may be formed between first electrode-side gap-forming part 23b and second electrode-side gap-forming part 24b. Additionally, nano-gap electrode pair 21 may comprise a nano-gap NG wherein, the leading end of first electrode-side gap-forming part 23b of first electrode part 23 may be disposed oppositely to base part 24a of the second electrode part 24, and second gap region NG4 may extend perpendicularly to substrate 2, the terminal end of second gap region NG4 may connect or overlap with first gap region NG3, wherein in first gap region NG3 may be formed between first electrode-side gap-forming part 23b and base part 24a.

Consequently, a nano-gap electrode pair 21 may be utilized to analyze a sample with high sensitivity by selecting a nano-gap NG between first electrode part 23 and second electrode part 24 to have a small width W1. A solution containing single stranded or double stranded DNA may pass through not only first gap region NG3 coplanar to substrate 2 but also second gap region NG4 disposed perpendicularly to substrate 2 wherein nano-gap NG between first electrode part 23 and second electrode part 24 may be selected to have a small width W1. Thus, a larger amount of solution may easily pass through nano-gap NG.

In some methods for manufacturing a nano-gap electrode pair 21, electrode-forming part 41 may be first formed on part of substrate 2 in a manner that provides a level difference between substrate 2 and first electrode-forming part 41. Then, conductive layer 26 may be formed on substrate 2 and first electrode-forming part 41, thus disposing conductive layer 26 extending in the coplanar to substrate 2 and perpendicularly to the substrate 2 at the edge of first electrode part 41. Subsequently, second electrode-forming part 42 may be formed on conductive layer 26, and then first electrode-forming part 41, conductive layer 26 and second electrode-forming part 42 may be patterned using resist masks 44 and 45.

Consequently, first electrode part 23 and second electrode part 24 may be formed having predetermined shapes. In some embodiments, a level difference may be formed whereby second electrode-side gap-forming part 24b of the second electrode part 24 overlaps first electrode-side gap-forming part 23b of first electrode part 23 on opposing sides of conductive layer 26, thereby forming conductive layer 26 extending coplanar to substrate 2 and perpendicularly to substrate 2 between first electrode part 23 and second electrode part 24. Finally, a portion of conductive layer 26 between first electrode part 23 and second electrode part 24 may be removed, thereby forming nano-gap NG composed of first gap region NG3 coplanar to substrate 2 and second gap region NG4 extending perpendicularly to substrate 2, the terminal end of second gap region NG4 connecting or overlapping with first gap region NG3, wherein first gap region NG is formed between the first electrode part 23 and the second electrode part 24.

In this way, it is possible to manufacture a nano-gap electrode pair 21 in which a solution can pass through not only first gap region NG3 but also second gap region NG4 even if a width W1 of nano-gap NG between first electrode part 23 and second electrode part 24 may be made substantially small, and therefore, a solution containing single stranded or double stranded DNA, which may be measured by one or both nano-gaps NG3 and NG4, may more easily pass through nano-gap NG.

In some embodiments utilizing a manufacturing method as described herein, it is possible to easily adjust width W1 of nano-gap NG between first electrode part 23 and second electrode part 24 simply by adjusting a film thickness of conductive layer 26. In addition, since conductive layer 26 may be formed to have an extremely thin film thickness; using this manufacturing method, it is possible to form a nano-gap NG (first gap region NG3 and second gap region NG4) having an extremely small width W1 corresponding to a film thickness of conductive layer 26.

In some embodiments it may be desirable to flow DNA through a nano-gap electrode pair(s). In some embodiments motion of DNA can be created by electrophoresis, electroosmotic flow or pressure driven flow. It may be desirable to orient DNA when passing through a nano-gap electrode pair(s) so one end enters first and a second end trails. It may also be desirable to insure that a significant percentage of DNA is directed through a nano-gap electrode pair(s), as opposed to traversing around the nanogap electrode pair(s). Therefore it may be desirable to integrate a closed channel structure to allow DNA to flow in a controlled manner through gap(s) of nanogap electrode pair(s). A channel can be made using lithographic techniques with a varying width. In some embodiments a channel may be fabricated with a varying depth using multiple masks. In some embodiments a separate cover may be added to an open channel integrated onto a substrate to create a closed channel. In some embodiments a cover may be transparent to allow inspection. In some cases the cover may be attached by adhesive, fusion bonding, Van der Waals forces, or physically clamped.

In other embodiments a closed channel can be integrated with a nano-gap electrode pair(s) chip using semiconductor processing. A closed channel can be made using lithographic techniques with a varying width. In some embodiments a closed channel may be fabricated with a varying depth using multiple masks. In some embodiments a closed channel can be created by wet etching a sacrificial layer. In other embodiments a sacrificial layer and etch reagent may be chosen so the sacrificial layer may be preferentially removed with a much faster etch rate than other material in contact with etch reagents.

In some embodiments a closed channel can have a narrow width and shallow depth dimensions near the nanochannel to help orient the DNA axially within the nanochannel. In order to reduce tangling of DNA, in some embodiments the narrow width and shallow depth can be less than 50x, less than 10x, less than 4x, less than 1x where x is the Kuhn length of DNA in the solution used in the sensor. The Kuhn length increases with lower ionic strength. In some cases the narrow width and/or narrow depth may be less than 1 micrometer, less than 500 nm, less than 200 nm, less than 100 nm, less than 50 nm or less than 20 nm.

In some cases a closed channel associated with a nano-gap electrode pair(s) can be integrated with a separate microfluidic structure. A microfluidic structure can be bonded or clamped to create a seal with a nano-gap electrode chip. In some embodiments a microfluidic structure may be one of metallic material, polymeric materials (e.g., polydimethylsiloxane, or PDMS) or glass. The microfluidic structure may be one of plastics or glass. In some embodiments a microfluidic structure may have branched channels and/or valves to help direct flow. In some embodiments a microfluidic structure may have integrated electrodes, for example to provide electrophoretic electrodes in an easily washed area.

In some embodiments multiple nano-gap electrode pair sensors may be incorporated into a nano-gap electrode chip. In some embodiments multiple nano-gap electrode pair sensors may connect with a covered channel of a nano-gap electrode chip. In some embodiments electronic circuitry for reading or controlling a nano-gap electrode chip may be fabricated on a substrate which may also comprise one or more nano-gap electrode pairs.

In some embodiments a closed channel can be created with nano-gap electrode pairs both parallel and perpendicular to the substrate wherein gaps associated with the nano-gap electrode pairs may be created by wet etching a material applied as a thin-film wherein the gap spacing may be substantially the same as a thin-film thickness. In some embodiments a closed channel can be combined with nano-gap electrode pairs parallel to a substrate wherein a gap may have been created by wet etching a material applied as a thin film, wherein a gap spacing may be substantially the same as a thin-film thickness. In other embodiments a closed channel can be combined with nano-gap electrode pairs perpendicular to a substrate wherein the closed channel may have been created by wet etching a material applied as a thin film wherein a gap spacing may be substantially the same as a thin-film thickness.

Figure 11A:
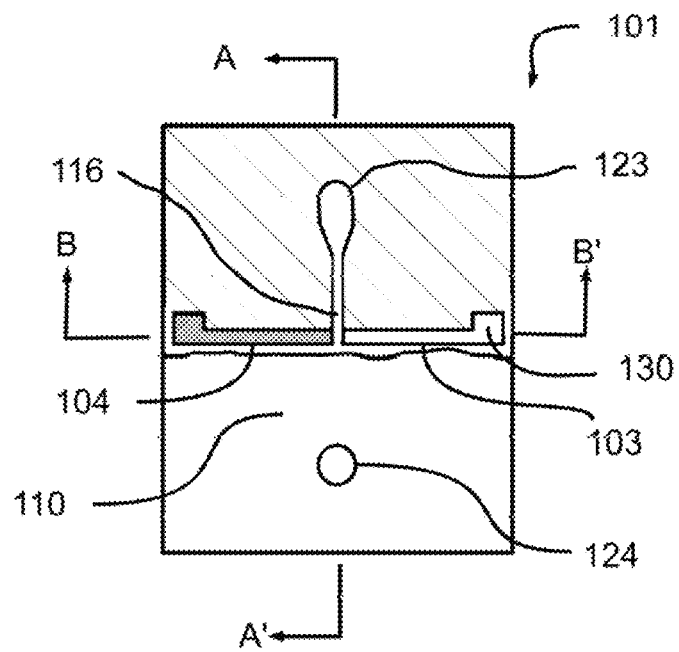
FIG. 11A is a schematic top view with a partial section view of a nano-gap electrode chip with an integrated nano-channel with the partial sectioned view cutting through the nanochannel plane.

FIG. 11A shows a top view of an embodiment of a nano-gap electrode chip 101 with the nanogap surfaces parallel to the substrate, and including an integrated fluidic channel. In FIG. 11A the top section is partially sectioned to the nanochannel center. In the top insulating layer 110, fluidic entry port 123 and fluidic exit port 124 connect to the nanochannel 116, which connects to outlet port 124. In the partial section, first nano-gap electrode 103 is adjacent to sacrificial material utilized to form nanochannel 116, which when removed will both create the gap and allow controlled sample introduction into the nano-gap. Second nano-gap electrode 104 is also adjacent to sacrificial material utilized to form nanochannel 116, but the nano-gap with gap spacing W2 is not visible in this view. The top insulating layer 110 may have access holes to connect to electrical connection pads 130 for section first nano-gap electrode 103 and second nano-gap electrode 104, or may have other interconnects as needed by associated circuitry (not shown), allowing for other embodiments wherein electrical connections may be made to electronic circuits on silicon substrate 108 layer.

Figure 11B:
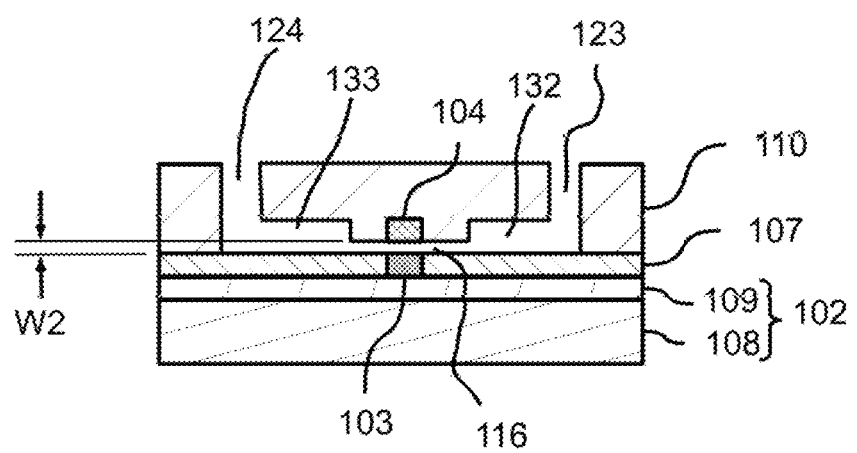
FIG. 11B is a schematic cross-sectional side view of a vertical cross-sectional configuration of a nano-gap electrode chip with an integrated nanochannel.

FIG. 11B shows a side view through vertical cross-section A-A' of FIG. 11A. In FIG. 11B a substrate 102 may comprise silicon substrate 108 and insulating layer 109. First nano-gap electrode 103 may form a nano-gap electrode pair with second nano-gap electrode 104 and nanochannel 116. Insulating layer 107 provides a planar surface for fabrication of nanochannel 116 thereupon. Insulating layer 110 provides a top surface for nanochannel 116, and provides a sealing surface for inlet port 123 and outlet port 124. In FIG. 11B shows a connection between inlet port 123 and optional thicker channel section 132, which may connect or be fluidically coupled to nanochannel 116. On the outlet side, nanochannel 116 can connect to an optional thicker channel section 133, which may connect to the outlet port 124. Gap spacing W2 is visible in this view.

In some embodiments fluid flow and/or movement of sample can be reversed. In some embodiments multiple nano-gap electrode pairs may intersect a nanochannel 116 allowing multiple measurements of a single DNA or RNA strand.

Figure 12A:
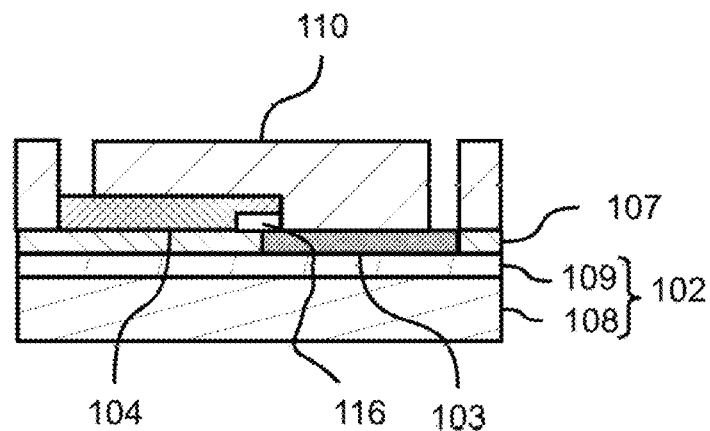
FIG. 12A is a schematic cross-sectional side view of a lateral cross-sectional configuration of a nano-gap electrode chip with an integrated nanochannel.

FIG. 12A shows a side view through lateral cross-section B-B' of FIG. 11A. First nano-gap electrode 103 is separated from second nano-gap electrode 104 by nanochannel 116. Insulating layer 107 provides a planar surface for nanochannel 116. Insulating layer 110 provides a top surface for nanochannel 116.

Figure 12B:
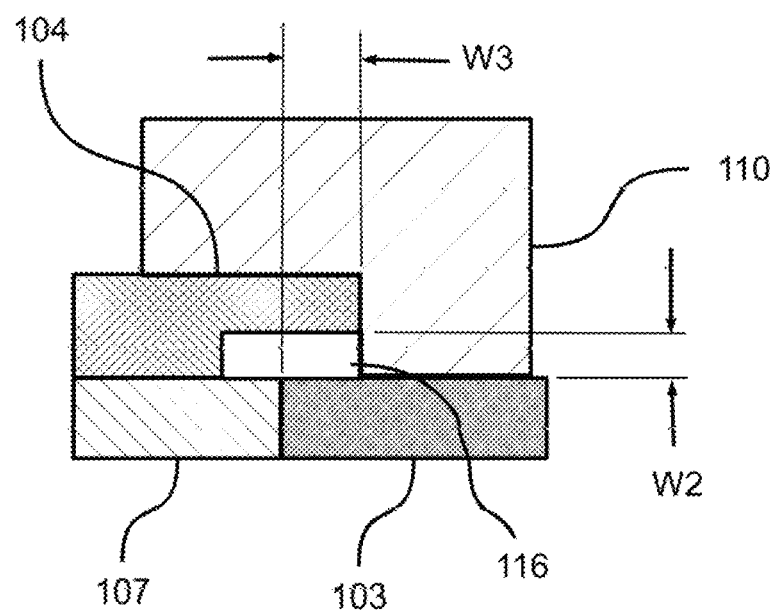
FIG. 12B is an enlarged schematic partial cross-sectional side view of the center section of FIG. 12A.

FIG. 12B shows an enlarged view of the nano-gap section of FIG. 12A. When sacrificial nano-gap layer 106 is etched away a nano-gap is formed between first nano-gap electrode 103 and second nano-gap electrode 104. Second nano-gap electrode 104 may overlap first nano-gap electrode 103 by overlap distance W3. In some embodiments overlap distance W3 may be less than 50 nm, less than 20 nm, less than 10 nm. Gap spacing W2 is also visible in this view.

Next as shown in FIG. 13A, a description will be made of a method for manufacturing a nano-gap electrode 101 of FIG. 11A, FIG. 11B, FIG. 12A and FIG. 12B. First, a substrate 102 for which, for example, silicon oxide layer 109, which may be formed on a silicon substrate 108, may be prepared. Then, an electrode-forming titanium nitride (TiN) film may be formed on the entire surface, or a portion thereof of silicon oxide layer 109 by, for example, a vapor phase deposition method (e.g., CVD).

Next, the electrode-forming layer is patterned using a photolithographic technique creating first nano-gap electrode 103, as illustrated in FIG. 13A and FIG. 13B showing lateral cross-section A-A' of FIG. 13A.

As illustrated in FIGS. 13C-13F in which constituent elements corresponding to those of 13A are denoted by like reference numerals and characters.

As illustrated in FIG. 13C, and FIG. 13D showing lateral cross-section B-B' of FIG. 13C, insulating layer 107 is applied, and then may be polished or overpolished using, for example, a planarization process, such as chemical mechanical polishing (CMP).

A thin nanochannel forming layer 106, which may be made from silicon nitride (SiN), may be formed on the entire surface by, for example, a vapor phase deposition method (e.g., CVD) and patterned using photolithographic techniques as illustrated in FIG. 13E, and FIG. 13F showing lateral cross-section C-C'.

Using a photolithographic technique an optional second nanochannel forming layer of SiN may be added to thin nanochannel forming layer 106.

Figure 14A:
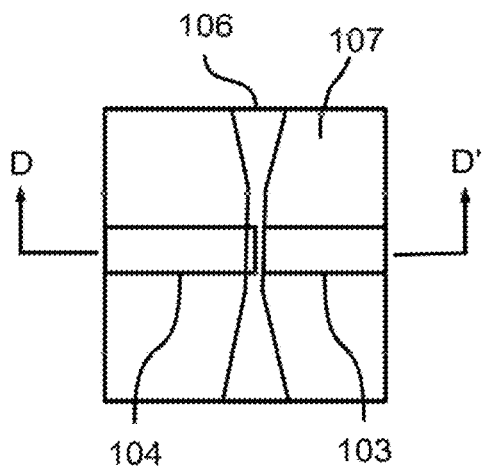
FIGS. 14A-14D are additional schematic views of a method for manufacturing the nano-gap electrode chip of FIG. 11A.
Figure 14B:
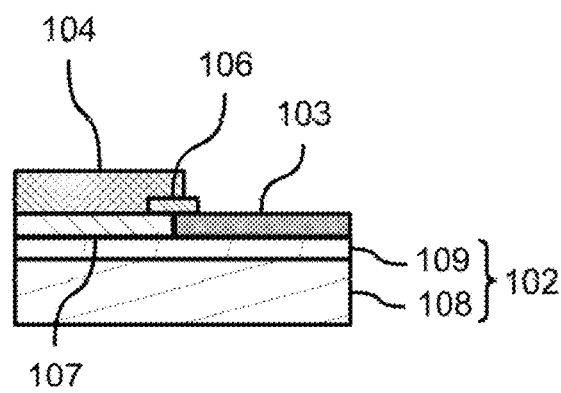
Figure 14C:
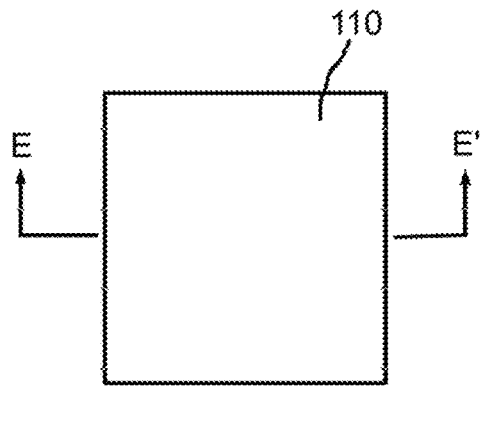
Figure 14D:
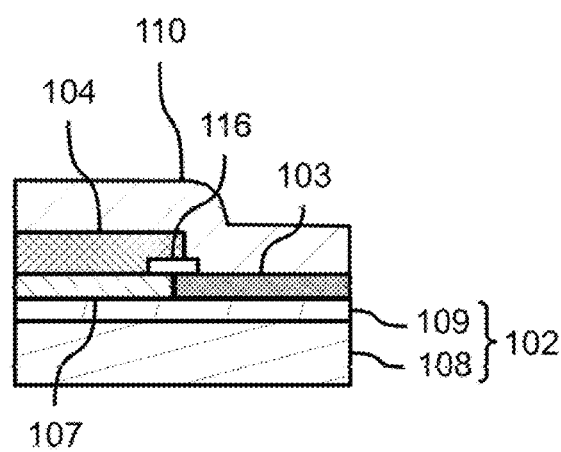

As illustrated in FIG. 14A and FIG. 14B, which shown a lateral cross-section along line D-D' of FIG. 14A, second nano-gap electrode 104 may be added using photolithographic techniques. An upper insulating layer 110 may be formed on surface of the structure, covering first nano-gap electrode 103, second nano-gap electrode, thin nanochannel forming layer 106, and insulating layer 107, by a vapor phase deposition for example, a vapor phase deposition method, wherein an access port and electrical pad access may be created utilizing photolithographic techniques. Any SiN features may then be wet etched, removing remaining portions of thin nanochannel forming layer, creating nanochannel 116 as shown in FIG. 14C and FIG. 14D, which shows a vertical cross-section along line E-E' of FIG. 14C.

In order to sequence individual bases it may be desirable to limit the number of atoms defining the gap. In some embodiments it may be desirable to have single atom tips on one or both sides of the gap. In some embodiments this may be done by using a naturally occurring tip or tip pair caused by surface roughness. In some embodiments the quality of a tip may be modified for better measuring quality or stability.

In some embodiments, a gap may be narrowed using an electrochemical method. The narrowing of the gap using an electrochemical method may proceed until the gap has reached a desired gap width, or a width greater or less than a desired gap width. A desired gap may have stable, generally monocrystalline tips on both sides. Single atom connections such that a conductance associated with a G0 ($2e^2/h$), corresponding to a resistance of, for example, 12.7K ohms for gold, may be used as intermediate state to creating a stable gap. Electrodeposited tips typically may be incapable of forming initially stable Go tips as described by Calvo et al in Physica status solidi (a), vol. 204, issue 6, pp. 1677-1685, and Boussaad et al in Appl. Phys. Lett. 80, 2398 2002, each of which is entirely incorporated herein by reference. Electromigration may be incapable of filling gaps wherein the gaps may have tunneling currents too low as to create sufficient electron wind as to cause movement of atoms within a tip.

An array of gaps spacings may be narrowed under software control executed by a computer processor, wherein a voltage may be applied and may be modified so as to effectuate an electrochemical deposition, and to control the rate of deposition, and thus the rate of narrowing of the gap. The current generated by the electrochemical process may be monitored, and the bias voltage may be modified and/or modulated so as to control the rate and/or progression of the gap narrowing.

An electrochemical deposition process may be unidirectional, or may be bidirectional, wherein a bias potential may be reversed so as to reverse the current flow and thus the deposition direction. A typical unidirectional electrodeposition process starting with two parallel nominally flat electrodes, which may comprise the same material, for instance, gold, platinum, tungsten, iridium or other metals, results in a structure wherein the cathode remains nominally flat, while the anode has a small sharp protrusion deposited thereupon. If it is desired to have a pair of electrodes wherein both of the pair of electrodes may have sharp tips, a unidirectional deposition method may be insufficient. A bidirectional electrodeposition process method may in some embodiments be utilized to create a pair of sharp tips, wherein the metal of the electrodes may be shuttled back and forth between the two electrodes, while the process causes a continuous sharpening of the tips as additional metal is "recruited" from flatter portions of the electrodes. The software may continuously or intermittently monitor the current levels of the electrodeposition process, and may reverse the polarity applied, either by reversing the sign of a potential applied to a first electrode, while the potential of a second electrode may remain fixed, or the potentials of the two electrodes may be reversed with respect to each other, while the absolute values may remain the same. In some embodiments the potentials reversals may be ramped up and/or down over a time interval. In some embodiments a potential difference may be different for one polarity than the other.

An electrodeposition method may utilize a variety of different fluids as a carrier, including deionized water, HCl, $KAu(CN)_2$, $KHCO_3$, KOH, and may use a deposition current at different periods during a deposition process which may include a current greater than about 10 μA, a current from about 5 microamp (μA) to 10 μA, a current from about 2 μA to 5 μA, a current from about 1 μA to 2 μA, or a current less than about 1 μA. A voltage source or a current source may be utilized to provide a potential so as to effectuate or facilitate an electrodeposition process. In some cases, a voltage source may apply a voltage greater than or equal to about 1 V, 2 V, 3 V, 4 V, or 5 V. In some embodiments, the concentration of the solutions used may be changed after an initial period of electrodeposition. In some embodiments an additional working electrode and/or reference electrode may be utilized as a part of the system so as to control the potential of the solution with respect to both electrodes of a nanogap electrode pair.

Tunneling current may be utilized to determine the width of nanogap electrode pair spacing, wherein the exponential current levels may be utilized to determine a spacing dimension. Tunneling current measurements may be made as a part of an electrodeposition process, or an electrodeposition process may be temporarily paused while a tunneling current measurement is made, and then the electrodeposition process may be restarted.

An electrodeposition process may be combined with an electromigration process, which may provide better control over the formation of a stable single atom tip or pair of tips. In electromigration, a current may be directed from one electrode to another electrode. For example, a constant current that is less than or equal to about 5 μA, 4 μA, 3 μA, 2 μA, or 1 μA may directed from one electrode to the other electrode at a variable voltage that is less than or equal to about 5 V, 4 V, 3 V, 2 V, or 1 V. Alternatively, a variable current that is less than or equal to about 5 μA, 4 μA, 3 μA, 2 μA, or 1 μA may directed from one electrode to the other electrode at a variable voltage that is less than or equal to about 5 V, 4 V, 3 V, 2 V, or 1 V.

In some embodiments an electromigration process may utilize a different fluidic environment than that used by an electromigration process. In some embodiments a fluidic environment may include aqueous reagents, organic reagents, a mixture of aqueous and/organic reagents, wherein the organic and aqueous reagents may be miscible, air, non-reactive gases or vacuum. An electrodeposition process may be utilized to form a gap which may be narrower than ultimately desired, and then an electromigration process may be utilized to widen the gap, and/or to form a more stable tip or pair of tips. The two processes may be interchanged, wherein an electrodeposition process may be utilized to, for example, create a tip gap spacing which may be narrower than ultimately desired, and an electromigration process may thence be utilized to create a more stable tip(s) and/or a tip spacing which may be a desired spacing, and may be utilized to provide a structure which may have a reduced number of crystal grain boundaries, particularly near the tips of a nanogap electrode pair. In some embodiments, a method may be utilized which combines simultaneous electrodeposition and electromigration.

In some embodiments, an electrodeposition method and an electromigration method may be utilized together to form a gap, wherein the electrodeposition method may remove material from a nanogap electrode pair which is joined, and an electromigration method may move material from one portion of the joined nanogap electrode pair to another portion of the joined nanogap electrode pair, such that the narrowest portion of the joined nanogap electrode pair may be further narrowed by the electromigration method. In other embodiments an electrodeposition method and an electromigration method may be utilized together to form a gap, wherein the electrodeposition method may remove material from a nanogap electrode pair which is joined, and an electromigration method may move material from one portion of the joined nanogap electrode pair to another portion of the joined nanogap electrode pair, such that the narrowest portion of the joined nanogap electrode pair may be further thickened by the electromigration method, potentially making the narrowed region of the joined nanogap electrode pair more crystalline. In other embodiments, an electrodeposition method and an electromigration method may be utilized together to form a gap, wherein the electrodeposition method may add material to a nanogap electrode pair which is joined, and an electromigration method may move material from one portion of the joined nanogap electrode pair to another portion of the joined nanogap electrode pair, such that the narrowest portion of the joined nanogap electrode pair may be further narrowed by the electromigration method.

In further embodiments, an electrodeposition method and an electromigration method may be utilized together to shape a gap, wherein the electrodeposition method may add material to a nanogap electrode pair which is separated, and an electromigration method may move material from one portion of the separated nanogap electrode pair to another portion of the joined nanogap electrode pair, such that the separation of the separated nanogap electrode pair may be further increased by the electromigration method. In other embodiments, an electrodeposition method and an electromigration method may be utilized together to shape a gap, wherein the electrodeposition method may remove material from a nanogap electrode pair which is separated, and an electromigration method may move material from one portion of the separated nanogap electrode pair to another portion of the joined nanogap electrode pair, such that the separation of the separated nanogap electrode pair may be narrowed by the electromigration method. In some embodiments, an electrodeposition method may deposit material on both sides of a nanogap electrode pair which has been separated, while in other embodiments an electrodeposition method may remove material from both sides of a nanogap electrode pair which has been separated, while in further embodiments, an electrodeposition method may remove material from one electrode of a nanogap electrode pair and may add material to the other electrode of a nanoelectrode pair. In some embodiments wherein both an electrodeposition method and an electromigration method are utilized together, a first method may be utilized for a period of time without the second method, and thence both methods may be utilized together for a period of time, and thence the second method may be utilized for a period of time without the first method. Any mixture or combination of methods may be utilized.

In some embodiment wherein an electrodeposition method may be utilized, a limiting resistor may be utilized so as to limit the removal of material. In other embodiments, the current may be monitored, and an applied potential may be limited such that a rate of material may be slowed and/or stopped, or slowed and then stopped based on the measured conductance, which may be a set ratio relative to a G0 of a material.

For an array of nanogap electrode pairs for which an electrodeposition and/or electromigration method is effectuated, control over individual voltages and/or measurements of individual nanogap electrode pairs may be performed simultaneously, or may be performed simultaneously for a set, for example a row or column of nanogap electrode pairs, or may be performed sequentially for each nanogap electrode pair. In some embodiments, a processor, which may be associated with a chip comprising nanogap electrode pairs, and may comprise A/D converters and/or digital-to-analog converter (DAC) circuits and/or transimpedance amplifiers, and/or integrating current monitors, or may be an external processor, may have insufficient capabilities to directly monitor and control all of the currents and voltages associated with the array of nanogap electrode pairs, thereby necessitating a sequential method, whereby one or a set of the nanogap electrode pairs may have one or more operations of a electrodeposition and/or electromigration process completed prior to completing one or more operations of the electrodeposition and/or electromigration process for other nanogap electrode pairs. For example, wherein an electrodeposition process may utilize multiple different fluidic reagents, for example using different concentrations, one or more operations utilizing a first reagent may be performed for a subset of the nanogap electrode pairs prior to performing the one or more operations for other nanogap electrode pairs, but all nanogap electrode pairs may have the same one or more operations performed prior to replacing one fluidic reagent with another reagent. In other embodiments wherein fluidic control may be effectuated using, for example, valves (e.g., microvalves or nanovalves) as a part of the array of nanogap electrode pairs, wherein one or more row or columns of nanogap electrode pairs may have a different reagent supplied thereto relative to other members of the nanogap electrode array, different operations may proceed to completion for different sets of a nanogap electrode pair array prior to replacing a first reagent with a second reagent for other members of the nanogap electrode pair array.

In some embodiments tip formation may be done at a wafer level. In some embodiments tip formation may be done at a chip level. In some embodiments tip formation may be done in a sequencing instrument to address tip stability issues. In some embodiments, tip formation and/or tip reformation may be performed as a part of user initiated method, such as a DNA sequencing assay.

In some embodiments, a nanogap electrode pair may be fabricated by forming a nanoaperture, which may be formed from a material different from a material used to form a nanogap electrode pair, wherein the nanoaperture may form a region which may subsequently become the gap of a nanogap electrode, and wherein the nanoaperture may be subsequently removed so as to allow access of the nanogap electrode pair to a sample fluid in a subsequent assay. In some embodiments, an electrodeposition method may be utilized wherein the nanoaperture may be formed over or proximate to a starting electrode, which may be a planar electrode, and further electrodeposition may connect the starting electrode to a second electrode. An electromigration process and/or electrodeposition may be utilized to (re)move material from the nanoaperture, forming a nanogap electrode pair.

In other embodiments a nanogap electrode may be formed by forming a nanoaperture, which may be formed at least in part by an anisotropic KOH 111 etch, and/or a focused ion beam etch, or another process suitable for fabrication of a nanoaperture, and may be formed from first material, such as silicon, but which may be any material compatible with the operations described herein. In a subsequent operation, a metal deposition may be performed so as to form the second electrode of a nanogap electrode pair. In some embodiments, an optional second material may be formed in an additional layer, such as silicon nitrate or any other appropriate material which may be remain in place during a removal process, which may be a wet etch, which removes the first material of the nanoaperture, may be utilized so as to form a two layer nanoaperture. In a subsequent operation, the silicon may be removed, at least in part, so as to allow fluidic access to the nanogap electrode pair, wherein the metal and the optional second material may remain. An electrodeposition and/or electromigration process may be utilized so as to separate the nanogap electrode pair, forming the nanogap of the nanogap electrode pair. A second material may be utilized so as to minimize fluidic contact with one electrode, thereby minimizing background current which may otherwise occur from the comparatively large surface area of first electrode. The size of the nanoaperture, while still needing reasonable tolerances, may have looser tolerance requirements than those needed in forming a nanoaperture useful for, for example, DNA sequencing using ion currents, as an electrodeposition and/or electromigration method used subsequently with feedback may be utilized to compensate for variation in nanoaperture size variations.

It should be noted that the present disclosure is not limited to the present embodiments, but may be modified and carried out in various other ways within the scope of the subject matter of the present invention. For example, various materials may be applied as materials for electrode parts 3 and 4 (23 and 24), substrate 2, insulating layer 6, conductive layer 26 serving as a gap-forming layer, insulating layer 7, resist masks 15, 44 and 45, and the like. In addition, each layer formed when manufacturing a nano-gap electrode pair 1, 21 may be formed using various other methods, as necessary, including a sputtering method.

In addition, in the above-described embodiments, a description has been made of nano-gap electrode pair electrodes in which single stranded or double stranded DNA may be passed through a nano-gap NG between the electrode, and the values of currents flowing across the electrode when bases of the single stranded or double stranded DNA pass through a nano-gap NG between the electrode parts may be measured with an ammeter. The present invention is not limited to these embodiments, however. A nano-gap electrode pair may be used in various other applications. Although in some cases single stranded and double stranded DNA has been described as a target for measurement, the present disclosure is not limited to such a target. It will be appreciated that other targets (e.g., RNA or protein) may be used. Various other types of fluids, including a liquid and a gas, may be utilized applied as a sample containing fluid. In addition, various other types of measurement targets, including viruses and bacteria, proteins and peptides, carbohydrates and lipids, organic and inorganic molecules, may be targeted for measurement.

Additionally, in the above-described embodiments, a case has been described in which insulating layer 6 (conductive layer 26) serving as a gap-forming layer is formed in a conformal manner. The present invention is not limited to these embodiments, however. For example, insulating layer 6 (conductive layer 26) may be changed in film thickness depending on the location of film formation by varying film-forming conditions (temperature, pressure, gas used, flow ratio, and the like), without film-forming the layer in a conformal manner.

If insulating layer 6 (conductive layer 26) is changed in film thickness depending on the location of film formation without film-forming the layer in a conformal manner, a nano-gap NG formed from insulating layer 6 (conductive layer 26) may have a different width between first gap region NG1 (NG3) coplanar to substrate 2 and second gap region NG2 (NG4) extending perpendicularly to substrate 2; the terminal end of second gap region NG2 (NG4) may connect or overlap with first gap region NG1 (NG3). For example, in the some embodiments, if a polymer contained in a photoresist is adhered to side surface 41*b* and conductive layer 26 is formed on side surface 41*b* such that when the first electrode-forming part 41 including side surface 41*b* is formed, a width across the gap-forming optionally apical surface 28*b* of first electrode part 23 and opposed-to-gap side surface 29*b* of second electrode part 24 may become larger by as much as the thickness of a polymer. As a result, a width of second gap region NG4 may be larger than a width of first gap region NG3. If a polymer is not adhered to side surface 41*b* of first electrode-forming part 41, film thickness of the conductive layer 26 formed on side surface 41*b* may be made thinner than a film thickness of conductive layer 26 formed on upper surface 41*a* by decreasing a degree of coverage by changing conditions of a vapor phase deposition method (e.g., CVD) at a time of forming conductive layer 26. As a result, a width of second gap region NG4 may be smaller than a width of first gap region NG3.

Even in this case, a solution can pass through not only first gap region NG1 (NG3) coplanar to substrate 2, but also through second gap region NG2 (NG4) extending perpendicularly to substrate 2, as in the above-described embodiments, even if nano-gap NG between first electrode part 3 (23) and second electrode part 4 (24) is selected to have a small width W1, and therefore, a solution containing single stranded or double stranded DNA as a measurement target may easily pass through nano-gap NG.

Base part 4*a* of second electrode part 4 may be disposed above thin-film part 3*a* of first electrode part 3 on insulating layers 6 and 7. In some cases, a film thickness of insulating layer 6 may be increased without forming insulating layer 7 so as to dispose base part 4*a* of second electrode part 4 above thin-film part 3*a* of first electrode part 3 only on insulating layer 6 serving as a gap-forming layer.

In some embodiments, a case has been described in which conductive layer 26 which may be made from an electroconductive material may be applied as a gap-forming layer. The present invention is not limited to this embodiment, however. An insulating layer made from an insulating material may be applied and utilized as a gap-forming layer.

Computer Control Systems

Figure 15:
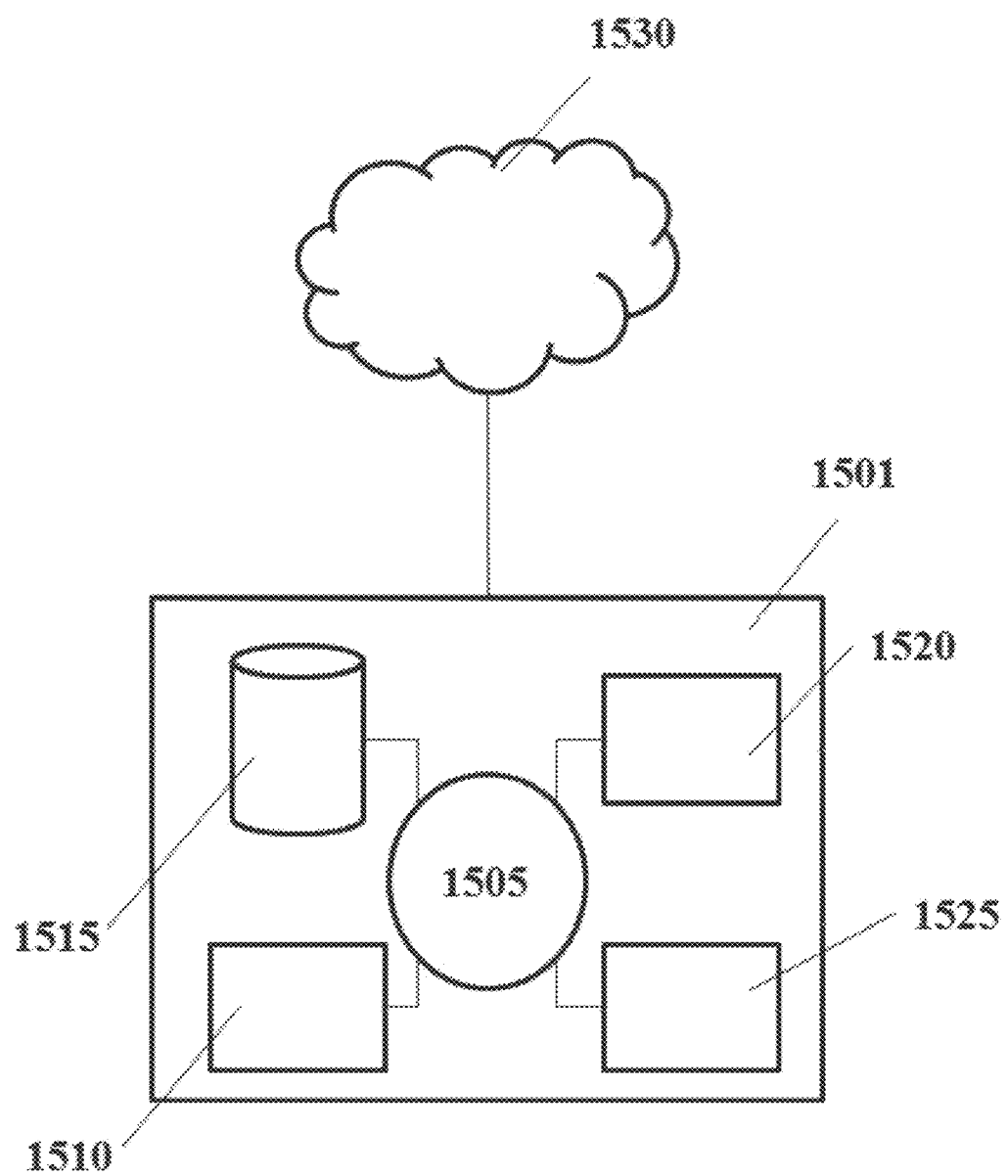
FIG. 15 shows a computer control system that is programmed or otherwise configured to implement devices, systems and methods of the present disclosure.

The present disclosure provides computer control systems that are programmed to implement methods of the disclosure. FIG. 15 shows a computer system 1501 that is programmed or otherwise configured to sequence a biomolecule, such as a protein. The computer system 1501 can be the control units 26 and 226 described elsewhere herein. The computer system 1501 includes a central processing unit (CPU, also "processor" and "computer processor" herein) 1505, which can be a single core or multi core processor, or a plurality of processors for parallel processing. The computer system 1501 also includes memory or memory location 1510 (e.g., random-access memory, read-only memory, flash memory), electronic storage unit 1515 (e.g., hard disk), communication interface 1520 (e.g., network adapter) for communicating with one or more other systems, and peripheral devices 1525, such as cache, other memory, data storage and/or electronic display adapters. The memory 1510, storage unit 1515, interface 1520 and peripheral devices 1525 are in communication with the CPU 1505 through a communication bus (solid lines), such as a motherboard. The storage unit 1515 can be a data storage unit (or data repository) for storing data. The computer system 1501 can be operatively coupled to a computer network ("network") 1530 with the aid of the communication interface 1520. The network 1530 can be the Internet, an internet and/or extranet, or an intranet and/or extranet that is in communication with the Internet. The network 1530 in some cases is a telecommunication and/or data network. The network 1530 can include one or more computer servers, which can enable distributed computing, such as cloud computing. The network 1530, in some cases with the aid of the computer system 1501, can implement a peer-to-peer network, which may enable devices coupled to the computer system 1501 to behave as a client or a server.

The CPU 1505 can execute a sequence of machine-readable instructions, which can be embodied in a program or software. The instructions may be stored in a memory location, such as the memory 1510. The instructions can be directed to the CPU 1505, which can subsequently program or otherwise configure the CPU 1505 to implement methods of the present disclosure. Examples of operations performed by the CPU 1505 can include fetch, decode, execute, and writeback.

The CPU 1505 can be part of a circuit, such as an integrated circuit. One or more other components of the system 1501 can be included in the circuit. In some cases, the circuit is an application specific integrated circuit (ASIC).

The storage unit 1515 can store files, such as drivers, libraries and saved programs. The storage unit 1515 can store user data, e.g., user preferences and user programs. The computer system 1501 in some cases can include one or more additional data storage units that are external to the computer system 1501, such as located on a remote server that is in communication with the computer system 1501 through an intranet or the Internet.

The computer system 1501 can communicate with one or more remote computer systems through the network 1530. For instance, the computer system 1501 can communicate with a remote computer system of a user. The user can access the computer system 1501 via the network 1530.

Methods as described herein can be implemented by way of machine (e.g., computer processor) executable code stored on an electronic storage location of the computer system 1501, such as, for example, on the memory 1510 or electronic storage unit 1515. The machine executable or machine readable code can be provided in the form of software. During use, the code can be executed by the processor 1505. In some cases, the code can be retrieved from the storage unit 1515 and stored on the memory 1510 for ready access by the processor 1505. In some situations, the electronic storage unit 1515 can be precluded, and machine-executable instructions are stored on memory 1510.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine (or computer) readable medium, such as computer-executable code (or computer program), may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Devices, systems and methods of the present disclosure may be combined with and/or modified by other devices, systems, or methods, such as those described in, for example, JP 2013-36865A, US 2012/0322055A, US 2013/0001082A, US 2012/0193237A, US 2010/0025249A, JP 2011-163934A, JP 2005-257687A, JP 2011-163934A and JP 2008-32529A, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for detecting a biomolecule, comprising:
    (a) directing a biomolecule to a nano-gap electrode device having a first electrode and a second electrode adjacent to said first electrode, wherein said first electrode is separated from said second electrode by a nano-gap that is dimensioned to permit said biomolecule to access said nano-gap, wherein said nano-gap has at least a first gap region and a second gap region, and wherein said second gap region is oriented at an angle that is greater than zero degrees with respect to a plane having said first gap region, wherein said first electrode comprises a first portion and a second portion that is adjacent to said first portion, wherein said first portion and said second portion are adjacent to a substrate, wherein said first portion has a surface that partially defines said second gap region, and wherein said second portion has a surface that partially defines said first gap region;
    (b) using said nano-gap electrode device to measure electrical signals upon said biomolecule accessing said nano-gap; and
    (c) detecting said biomolecule using said electrical signals measured in (b).

2. The method of claim 1, wherein said first portion has a greater thickness than said second portion.

3. The method of claim 1, wherein said detecting comprises comparing said electrical signals to reference signals that are indicative of said biomolecule or a portion thereof.

4. The method of claim 1, wherein said detecting comprises identifying said biomolecule or a portion thereof.

5. The method of claim 1, wherein said biomolecule is a nucleic acid molecule, and wherein said detecting in (c) comprises sequencing said nucleic acid molecule.

6. The method of claim 1, wherein said electrical signals include electrical current, wherein said electrical current is tunneling current.

7. The method of claim 1, wherein said second gap region is oriented at an angle that is about 90° with respect to said plane having said first gap region.

8. The method of claim 1, wherein a portion of said first electrode or said second electrode has a single atom tip.

9. The method of claim 1, wherein said biomolecule is directed to said nano-gap through at least one channel that is in fluid communication with said nano-gap.

10. The method of claim 1, wherein said nano-gap electrode device is part of an array of independently addressable nano-gap electrode devices.

11. The method of claim 1, wherein upon said biomolecule accessing said nano-gap, a portion of said biomolecule accesses said first gap region and a remainder of said biomolecule accesses said second gap region.

12. A method for manufacturing nano-gap electrodes for use in detecting a biomolecule, comprising:
    (a) providing a first electrode-forming part adjacent to a substrate;
    (b) forming a gap-forming layer adjacent to a surface of said first electrode-forming part;
    (c) forming a second electrode-forming part adjacent to said gap-forming layer; and
    (d) removing a portion of said gap-forming layer to form a nano-gap between said first electrode part and said second electrode part, wherein said nano-gap is dimensioned to permit said biomolecule to access said nano-gap, wherein said nano-gap has at least a first gap region and a second gap region, wherein said second gap region is oriented at an angle that is greater than zero degrees with respect to a plane having said first gap region, wherein said first electrode-forming part comprises a first portion and a second portion that is adjacent to said first portion, wherein said first portion and said second portion are adjacent to a substrate, wherein said first portion has a surface that partially defines said second gap region, and wherein said second portion has a surface that partially defines said first gap region.

13. The method of claim 12, further comprising, subsequent to (c), exposing a surface of said first electrode-forming part, a surface of said second portion of said gap-forming layer, and a surface of said second electrode-forming part.

14. The method of claim 13, further comprising patterning said second electrode-forming part, said gap-forming layer and said first electrode-forming part to provide a first electrode part and a second electrode part each having a predetermined shape.

15. The method of claim 12, wherein said second gap region is oriented at an angle that is greater than about 25° with respect to said plane having said first gap region.

16. The method of claim 12, further comprising processing said first electrode part or said second electrode part to have a single atom tip.

17. The method of claim 12, wherein (a) comprises forming an insulating layer adjacent to a portion of said electrode-forming part having a lower thickness than another portion of said electrode-forming part, and forming said gap-forming layer adjacent to said insulating layer.

18. The method of claim 12, wherein a terminal end of said second gap region is coupled to said first gap region.

19. The method of claim 12, wherein said first electrode-forming part has a level difference on said substrate.

20. The method of claim 12, wherein said first gap region is parallel to said substrate.

* * * * *